United States Patent
Sacha et al.

(10) Patent No.: US 10,302,632 B2
(45) Date of Patent: *May 28, 2019

(54) MACROMOLECULAR CONJUGATES FOR VISUALIZATION AND SEPARATION OF PROTEINS AND CELLS

(71) Applicants: USTAV ORGANICKE CHEMIE A BIOCHEMIE AV CR, V.V.I., Prague (CZ); USTAV MAKROMOLEKULARNI CHEMIE AV CR, V.V.I., Prague—Brevnov (CZ); UNIVERZITA KARLOVA V PRAZE, PRIRODOVEDECKA FAKULTA, Prague (CZ)

(72) Inventors: Pavel Sacha, Prague (CZ); Jan Konvalinka, Prague (CZ); Jiri Schimer, Prague (CZ); Tomas Knedlik, Koprivnice (CZ); Vaclav Navratil, Prague (CZ); Jan Tykvart, Kromeriz (CZ); Frantisek Sedlak, Prague (CZ); Pavel Majer, Prague (CZ); Petr Cigler, Prague (CZ); Vladimir Subr, Melnik (CZ); Karel Ulbrich, Prague (CZ); Jiri Strohalm, Prague (CZ)

(73) Assignees: USTAV ORGANICKE CHEMIE A BIOCHEMIE AV CR, V.V.I., Prague (CZ); USTAV MAKROMOLEKULARNI CHEMIE AV CR, V.V.I., Prague (CZ); UNIVERZITA KARLOVA V PRAZE, PRIRODOVEDECKA FAKULTA, Prague (CZ)

( * ) Notice: Subject to any disclaimer, the term of this patent is extended or adjusted under 35 U.S.C. 154(b) by 0 days.

This patent is subject to a terminal disclaimer.

(21) Appl. No.: 16/128,982

(22) Filed: Sep. 12, 2018

(65) Prior Publication Data

US 2019/0033300 A1 Jan. 31, 2019

Related U.S. Application Data

(63) Continuation of application No. 15/541,824, filed as application No. PCT/CZ2016/050003 on Jan. 13, 2016, now abandoned.

(30) Foreign Application Priority Data

Jan. 14, 2015 (CZ) .................................... 2015-20

(51) Int. Cl.
  *A61K 9/00* (2006.01)
  *G01N 33/534* (2006.01)
  (Continued)

(52) U.S. Cl.
  CPC ........... *G01N 33/534* (2013.01); *A61K 47/58* (2017.08); *A61K 49/0054* (2013.01);
  (Continued)

(58) Field of Classification Search
  CPC ..................................................... G01N 33/534
  See application file for complete search history.

(56) References Cited

FOREIGN PATENT DOCUMENTS

| EP | 0245926 A2 | 11/1987 |
|----|------------|---------|
| WO | 2004009136 A2 | 1/2004 |
| WO | 2005007798 A2 | 1/2005 |

OTHER PUBLICATIONS

International Search Report and Written Opinion for corresponding PCT application No. PCT/CZ2016/050003, dated Jul. 27, 2016.
(Continued)

*Primary Examiner* — Paul W Dickinson
(74) *Attorney, Agent, or Firm* — Notaro, Michalos & Zaccaria P.C.

(57) ABSTRACT

A macromolecular water-soluble conjugates based on synthetic copolymers to which at least one affinity tag, at least one imaging probe and at least one targeting ligand are
(Continued)

bound via covalent bonds. The macromolecular conjugate may be used in identification, visualization, quantification or isolation of proteins and/or cells.

9 Claims, 13 Drawing Sheets

Specification includes a Sequence Listing.

(51) Int. Cl.
C08F 220/58 (2006.01)
G01N 33/531 (2006.01)
G01N 33/532 (2006.01)
G01N 33/533 (2006.01)
A61K 49/00 (2006.01)
A61K 47/58 (2017.01)

(52) U.S. Cl.
CPC ......... C08F 220/58 (2013.01); G01N 33/531 (2013.01); G01N 33/532 (2013.01); G01N 33/533 (2013.01); C08F 2500/01 (2013.01)

(56) References Cited

OTHER PUBLICATIONS

Kopecek, "HPMA copolymers: Origins, early developments, present, and future," Advanced Drug Delivery Reviews, 2010, 62(2), 122-149 (Year: 2010).

Hart, "HPMA copolymer-modified Avid in: Immune Response," Journal of Biomaterials Science, Polymer Edition, 2000, 11, 1-12 ( Year: 2000).

Zarabi, "Macrophage targeted N-(2-hydroxypropyl) methacrylamide conjugates for magnetic resonance imaging," Molecular Pharmaceutics, 2006, 3(5), 550-557 (Year: 2006).

Tau, "Multifunctional pH-Disintegrable micellar nanoparticles of asymmetrically functionalized-cyclodextrin-based star copolymer covalently conjugated and doxorubicin and DOTA-Gd moieties," Biomaterials, 2012, 33, 2521-2531 (Year: 2012).

Brandon, "In Vitro Evaluation of HPMA-Copolymers Targeted to HER2 Expressing Pancreatic Tumor Cells for Image Guided Drug Delivery," Macromolecular Bioscience, 2013, 14, 92-99 (Year: 2013).

Borgman, "Tumor-targeted HPMA copolymer-(RGDfk)-(CHX-A"-DTPA) conjugates show increased kidney accumulation," Journal of Controlled Release, 2008, 132(3), 193-199 (Year: 2008).

Buckway, "Overcoming the stromal barrier for targeted delivery of HPMA copolymers to pancreatic tumors," International Journal of Pharmaceutics, 2013, 456, 202-211 (Year: 2013).

Fernandez-Megia, "Conjugation of bioactive ligands to PEG-grafted chitosan at the distal end of PEG," Macromolecules, 2007, 8(3), 833-842 (Year: 2007).

SEQUENCE LISTING

```
<160> NUMBER OF SEQ ID NOS: 8

<210> SEQ ID NO 1
<211> LENGTH: 8
<212> TYPE: PRT
<213> ORGANISM: Artificial
<220> FEATURE:
<223> OTHER INFORMATION: FLAG tag

<400> SEQUENCE: 1

Asp Tyr Lys Asp Asp Asp Asp Lys
1               5

<210> SEQ ID NO 2
<211> LENGTH: 9
<212> TYPE: PRT
<213> ORGANISM: Artificial
<220> FEATURE:
<223> OTHER INFORMATION: HA tag

<400> SEQUENCE: 2

Tyr Pro Tyr Asp Val Pro Asp Tyr Ala
1               5

<210> SEQ ID NO 3
<211> LENGTH: 8
<212> TYPE: PRT
<213> ORGANISM: Artificial
<220> FEATURE:
<223> OTHER INFORMATION: Strep-tag

<400> SEQUENCE: 3

Trp Ser His Pro Gln Phe Glu Lys
1               5
```

```
<210> SEQ ID NO 4
<211> LENGTH: 10
<212> TYPE: PRT
<213> ORGANISM: Artificial
<220> FEATURE:
<223> OTHER INFORMATION: c-myc-tag

<400> SEQUENCE: 4

Glu Gln Lys Leu Ile Ser Glu Glu Asp Leu
1               5                   10

<210> SEQ ID NO 5
<211> LENGTH: 14
<212> TYPE: PRT
<213> ORGANISM: Artificial
<220> FEATURE:
<223> OTHER INFORMATION: V5-tag

<400> SEQUENCE: 5

Gly Lys Pro Ile Pro Asn Pro Leu Leu Gly Leu Asp Ser Thr
1               5                   10

<210> SEQ ID NO 6
<211> LENGTH: 13
<212> TYPE: PRT
<213> ORGANISM: Artificial
<220> FEATURE:
<223> OTHER INFORMATION: E-tag

<400> SEQUENCE: 6

Gly Ala Pro Val Pro Tyr Pro Asp Pro Leu Glu Pro Arg
1               5                   10

<210> SEQ ID NO 7
<211> LENGTH: 15
<212> TYPE: PRT
<213> ORGANISM: Artificial
<220> FEATURE:
<223> OTHER INFORMATION: S-tag

<400> SEQUENCE: 7

Lys Glu Thr Ala Ala Ala Lys Phe Glu Arg Gln His Met Asp Ser
1               5                   10                  15

<210> SEQ ID NO 8
<211> LENGTH: 6
<212> TYPE: PRT
<213> ORGANISM: Artificial
<220> FEATURE:
<223> OTHER INFORMATION: chromogenic substrate

<400> SEQUENCE: 8

Lys Ala Arg Val Glu Ala
1               5
```

MACROMOLECULAR CONJUGATES FOR VISUALIZATION AND SEPARATION OF PROTEINS AND CELLS

CROSS REFERENCE TO RELATED APPLICATIONS

This is a continuation application of U.S. patent application Ser. No. 15/541,824, filed Jul. 6, 2017 which is a U.S. National Phase of International Application No. PCT/CZ2016/050003, filed Jan. 13, 2016, which are both incorporated herein by reference, and which claims priority on Czech Republic patent application No. PV 2015-20, filed Jan. 14, 2015, which priority claim is repeated here.

FIELD OF ART

The invention describes synthetically prepared macromolecules having properties of monoclonal antibodies, said macromolecules being capable of replacing the use of antibodies in scientific research, in diagnostics, in biochemical investigations and for the preparation of targeted drugs. These synthetic macromolecules, targeted and binding specifically to certain proteins, are suitable for the visualization, identification and isolation of biomolecules and/or cells in biochemistry, molecular biology and medicine and as targeting ligands in the pharmacy and diagnostics.

BACKGROUND ART

The discovery and the subsequent use of monoclonal antibodies allowing detection and specific binding of biologically important molecules caused a revolution in biochemistry and molecular biology as well as in the diagnosis and treatment of numerous serious diseases. In science, this discovery led to the development of many important techniques today considered routine, such as Western blotting, immunohistochemistry, immunoprecipitation, flow cytometry or (confocal) microscopy. The ability of antibodies to specifically bind to (macro)molecules has led to their use as therapeutic agents, which can act either alone or after conjugation with a particular biologically active compound. Therapy with monoclonal antibodies has achieved significant success in the treatment of many different diseases, particularly various types of autoimmune disorders and various types of cancer [1]. There are currently over 40 monoclonal antibodies that are approved by FDA, and used in therapy [2].

Despite considerable success, the use of monoclonal antibodies has also some disadvantages. First, the production of antibodies is very expensive. As antibodies are large molecules of glycosylated proteins containing disulfide bonds, their production is bound to a eukaryotic expression system, which allows to perform said post-translational modifications. Like other proteins, antibody molecules are susceptible to degradation: generally they must be stored at low temperatures, and if necessary, frozen in aliquots. Their repeated thawing often leads to loss of their ability to bind a given antigen. Another disadvantage is their own creation and method of preparation, since the immunization of an animal may not always lead to successful production of antibodies—they often may not be produced at all, or can be non-specific to the antigen. Another disadvantage is the fact that for a close group of enzymes (ie. homologs, either paralogs or orthologs), it is often impossible to use the same antibody (recognizing native proteins) due to differences in amino acid residues on their surface.

A polymer formed by homopolymerization of N-(2-hydroxypropyl)methacrylamide (HPMA) is non-toxic, biocompatible, nonimmunogenic and water-soluble. It was originally designed for use as synthetic blood plasma substitute; at present, due to their properties, HPMA copolymers are used as carriers in the development of polymeric drugs and imaging compounds, in particular various types of anticancer drugs [3-4]. Most HPMA copolymers are multivalent macromolecules enabling the covalent attachment of multiple types of low molecular weight compounds such as drugs, radionuclides or fluorescent probes. Likewise, they also permit the binding of various macromolecules, e.g. (glyco)proteins, oligonucleotides and polynucleotides. Multivalency of these copolymers allows to connect both to only one type of molecules and to combinations of different molecules [5-7].

The present invention combines the advantages of a specific targeting of proteins by means of their specific ligands with the versatility and stability of the polymer chain.

DISCLOSURE OF THE INVENTION

The present invention provides a macromolecular conjugate of a synthetic copolymer with three types of low molecular weight functional compounds (hereinafter also referred to as "functional groups", i.e., "affinity tag", "imaging probe" and "targeting ligand"; this designation refers to their function in the final conjugate and has nothing to do with the so-called chemical functional groups). Synthetic copolymer forms the backbone of macromolecular conjugate to which molecules of functional groups are linked via a covalent bond: (a) affinity tag, (b) imaging probe, which may be for example a fluorescent compound, a radionuclide or a metal complex, (b) targeting ligand allowing specific targeting of this conjugate to a given protein. Targeting ligand is attached to the polymer chain via a flexible link. FIG. 1 schematically shows such conjugate.

The synthetic copolymer is preferably water-soluble.

Preparation of synthetic copolymers has been described previously [7-8]; said polymers contain the following monomers:

at least one type of monomer of Formula 1:

wherein:
$R^1$ is selected from H, $CH_3$;
$R^2$ is selected from $NH_2$, $NH-CH_2-CH(OH)-CH_3$, $NH-CH_3$, $NH-CH_2CH_3$, $NH-CH_2CH_2-OH$, $NH-CH_2CH_2CH_2-OH$, $NHC(CH_2OH)_3$, $NH-CH_2CH_2-N^+(CH_3)_3Cl^-$, $O-CH_2CH_2-OH$, $O-(CH_2CH_2O)_2-H$, $O-(CH_2CH_2O)_3-H$, $O-CH_2CH_2-N^+(CH_3)_3Cl^-$, $NH-(CH_2)_3N^+(CH_3)_2-(CH_2)_2-COO^-$;

and at least one type of monomer of Formula 2:

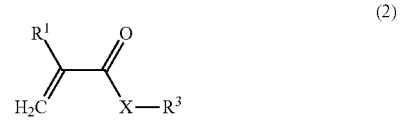

wherein:
R¹ is selected from H, CH₃, and
X is selected from NH—(CH₂)₂—CO, NH—(CH₂)₃—CO, NH—(CH₂)₄—CO, NH—(CH₂)₅—CO, Gly, GlyGly, GlyPheLeuGly, and
R³ is selected from

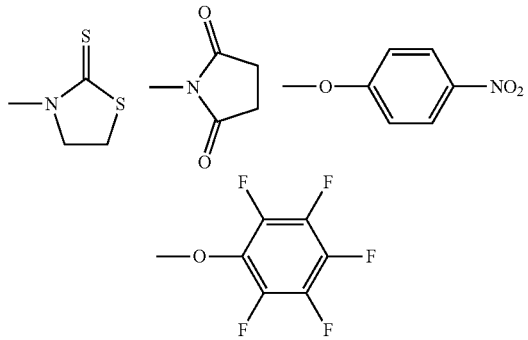

(R³ is a reactive group).

Content of the reactive groups (i.e. content of the monomer of Formula 2) in the copolymer is preferably in the range of 0.5 to 30 mol. %, more preferably 2 to 20 mol. %.

In the polymer conjugate, at least one reactive group R³ is replaced by a targeting ligand, at least one reactive group R³ is replaced by an affinity tag, and at least one reactive group R³ is replaced by an imaging probe. Preferably, more than one reactive group R³ is replaced by said groups. More preferably, more than 50% of the reactive groups R³ are replaced by the said groups, even more preferably, 100% of the reactive groups R³ are replaced by the said groups. Reactive groups remaining in the polymer chain after conjugation are always replaced by 1-amino-propan-2-ol group.

HPMA copolymer, i.e. poly(HPMA-co-Ma-β-Ala-TT); copolymer prepared by conventional radical solution copolymerization, or controlled radical copolymerization (e.g. RAFT-copolymerization, reversible addition-fragmentation chain-transfer) of N-(2-hydroxypropyl)methacrylamide (HPMA) and 3-(3-methakrylamidopropanoyl)thiazolidin-2-thione (Ma-β-Ala-TT), can be preferably used as the basic copolymer. HPMA content is preferably in the range from 70 to 98 mol %, the content of reactive thiazolidine-2-thione groups is preferably 2 to 30 mol %.

The functional compounds are attached to the polymer chain via an amide bond, which is formed in the reaction of the amino group present in the molecule of the functional compound, i.e. the affinity tag, the imaging probe and the targeting ligand, with the reactive group (preferably thiazolidine-2-thione) present on the polymer chain.

The molecular weight of the conjugate is preferably in the range of 1000 to 500000 g/mol, preferably in the range of 20000 to 150000 g/mol.

The affinity tag can be for example biotin. Using the very strong interaction biotin-avidin/streptavidin/neutravidin, the conjugate can be easily and specifically immobilized on various types of resins based on Streptravidin Sepharose, whereby it is possible to separate the conjugate from the mixture either by centrifugation or magnetic interaction (depending on the type of resin). Since the interaction of biotin with avidin/streptavidin/neutravidin is very strong ($K_D \sim 10^{-15}$), there is practically no risk of dissociation of the conjugate from the resin. Biotin can also be used for binding other proteins which are conjugated with streptavidin (either chemically or by genetic fusion)—e.g. neutravidin conjugated to horseradish peroxidase, which can be used for example in ELISA.

Besides biotin, also for example His tag (polyhistidine sequence, frequently six histidines in succession, bound with complex of chelating agent and nickel), FLAG tag (DYKDDDDK sequence recognized by an antibody), hemagglutinin tag (YPYDVPDYA amino acid sequence derived from the surface glycoprotein of the influenza virus, hemagglutinin, recognized by an antibody), Strep-tag (WSHPQFEK octapeptide sequence bound by modified streptavidin—Strep-Tactin), Avi-tag (peptide sequence recognized by biotin ligase; biotinylation enables subsequent isolation by streptavidin), GST (glutathione-S-transferase, the glutathione binding enzyme), c-myc-tag (EQKLISEEDL peptide sequence recognized by an antibody), V5-tag (GKPIPNPLLGLDST peptide sequence recognized by an antibody), E-tag (GAPVPYPDPLEPR peptide sequence recognized by an antibody), S-tag (KETAAAKFERQHMDS peptide sequence recognized by an antibody), SBP-tag (longer peptide sequence bound by streptavidin), poly(Glu)-tag (polyglutamate sequence, e.g. hexaglutamate that binds to anion exchangers), calmodulin tag (longer peptide sequence bound by calmodulin) or any other compound capable of immobilization to a solid phase can be the affinity tag.

The imaging probe may be a fluorophore, preferably the ATTO488 fluorophore, enabling visualization of the polymer and the particles or cells to which the conjugate is bound. This makes it possible to use the conjugate in methods such as e.g. flow cytometry (and a derived FACS technique, fluorescence-activated cell sorting, separating cells based on their fluorescence at a given wavelength), or immunocytochemistry and immunohistochemistry. For in vivo imaging, fluorophores with emission of radiation in the far red region of the spectrum ("far-red" fluorescence), e.g. DY676, can be advantageously used, as radiation with a longer wavelength passes through the tissue better than radiation of shorter wavelength.

In another embodiment of the invention (nuclear magnetic resonance, MRI), the imaging probe may be a metal complex, e.g. lanthanide (particularly Gd, Mn, or. Dy, Eu). In another embodiment (positron emission tomography, PET), the imaging probe may be a complex of a radionuclide, e.g. selected from the group consisting of $^{64}Cu$, $^{68}Ga$, $^{18}F$. In another embodiment (single photon emission computed tomography, SPECT), the imaging probe may be a complex of a radionuclide selected from the group $^{99m}Tc$, $^{123}I$, $^{125}I$, $^{131}I$, $^{57}Co$, $^{51}Cr$, $^{67}Ga$, $^{64}Cu$, $^{111}In$, $^{90}Y$. Ligands suitable for complexation of metals referred to are well known in the field, such as macrocyclic ligands, derivatives of cyclopentadienyl, phosphine and azine ligands. In another embodiment (electrochemiluminescence), the imaging probe may be a ruthenium complex $[Ru(Bpy)_3]^{2+}$.

Targeting ligand, a low-molecular substance, provides specific targeting of the whole conjugate to a given (desired) protein. Targeting ligand may be an inhibitor or substrate of an enzyme, receptor agonists or antagonists, a ligand of a protein carrier or another substance or compound capable of selectively binding to a particular protein or peptide sequence. When using a low molecular weight compound binding a specific protein, the targeting specificity of the resulting conjugate is given mostly by the properties of the low molecular weight compound. Since the targeting ligand is usually bound to a site performing certain biological functions, this binding requires a biologically active protein, i.e. in its native conformation. This allows, in contrast to large amounts of antibodies binding an epitope sequence, to distinguish between biologically active and inactive form of the enzyme.

Targeting ligand may be attached to the synthetic copolymer via a flexible linker, based on e.g. (oligo)polyethylene glycol, peptide, nucleic acid or oligosaccharide. The linker allows inhibitor binding to the active site of the enzyme so as to avoid steric hindrance of the binding by the polymer and time such linker allows targeting enzymes with active site hidden in the binding cavity of the enzyme. Preferably, the linker is selected from the group consisting of linkers based on polyethylene glycol, peptide, preferably a peptide having a molecular weight from 100 to 5000 g/mol, or nucleic acid, preferably a nucleic acids comprising 1 to 40 nucleotides, or oligosaccharide, preferably an oligosaccharide containing 1 to 40 monosaccharides.

Compared to currently used antibodies, synthetic molecules provided by this invention provide several advantages. Preparation of polymeric conjugates is inexpensive, and in comparison to antibodies, if there is an inhibitor of the enzyme, conjugates are also relatively easily prepared. Polymeric conjugates are chemically substantially more stable and their solutions can be repeatedly frozen and thawed without significant influence on their ability to bind the enzyme. One of the biggest advantages of these conjugates is that due to the present inhibitor they bind to the active site of the enzyme and thus bind only to enzymatically active form of the enzyme, i.e. always to a native protein. Antibodies lack this ability. Another advantage is the "non-biological" origin of the polymeric backbone—in many methods with complex matrices (e.g. immunoprecipitation from blood plasma, etc.) there is competition between endogenous antibodies or other proteins and the respective antibodies used in the experiment, which often leads to a reduction in the success of the experiment down to impracticability (e.g. frequent emergence of false positive results in ELISA). Polymeric conjugates, being synthetic molecules based on an entirely different structural pattern, do not cause these problems and can be used without side effects. Equally important is the fact that the active site of the enzyme is usually the most conserved point of the whole enzyme; this makes it possible to use one inhibitor (and therefore one conjugate) for a whole group of enzymes. This group may be relatively small (e.g. homologous proteins; two paralogs in the same organism, or orthologs in two different organisms), but it can also be e.g. an entire type of enzymes (aspartate proteases, etc.). We can never achieve this with antibodies, since they bind only the surface of enzymes, i.e. a highly variable part.

The principal advantage of the polymer conjugate system is its modularity. Since the individual functional compounds are connected to the polymer backbone via an amide bond formed by reaction of an amino group present on the functional compound with the reactive group (e.g. thiazolidine-2-thione) present on the polymer, the polymer chain can be substituted as needed. For example fluorophores may be replaced with others (if they contain an amino group) according to the desired wavelength. It is also possible to have several types of fluorophores on one polymer chain. The advantage is then rather the presence of several different inhibitors on one polymer than more fluorophores. This will ensure the specificity of the conjugate against two (or more) enzymes using one conjugate.

The examples of this patent describe methods that are commonly used in biochemistry and molecular biology, and they use antibodies. It is an ELISA, immunoprecipitation (or 'pull-down' if the substance is not of an antibody character), immunocytochemistry, Western blotting, flow cytometry and surface plasmon resonance. Methods have been chosen to illustrate the wide possibilities of use of such polymer conjugates and demonstration of modularity and versatility of this approach.

ELISA (Enzyme-Linked Immunosorbent Assay) is an immunoassay method, which due to its sandwich configuration with two different substances permits quantification of the protein amounts. First, a primary antibody against the protein is adsorbed to the surface of the plate and unoccupied surface of the plate is blocked with a solution of casein. Sample of the protein to be determined is then added, and after its binding to the antibody, the polymer conjugate capable of binding to this protein is added. The amount of the bound conjugate may be determined using Neutravidin (horseradish peroxidase-conjugated) binding biotin present on the conjugate. Besides this (chemiluminescent) method of determining the amount of the conjugate, its concentration can also be determined by fluorescence using fluorophores present on the conjugate. Alternatively to the above ELISA procedure, the polymer conjugate can also be immobilized by binding to neutravidin/streptavidin adsorbed on the surface of the plate (through biotin-streptavidin bond). After binding of the protein to be determined, the primary antibody against the protein is added, and its amount is then determined using a secondary antibody conjugated to horseradish peroxidase. Biotin present on the conjugate can thus be used both for immobilization and for detection, while a fluorophore only for detection.

From the above it is clear (as polymer conjugates bind specifically to the protein via targeting ligand) that it is possible to use this principle for testing various substances. In the first method, where the studied protein is bound to adsorbed primary antibody, the mixture of conjugate and a potential "inhibitor" (not necessarily an inhibitor in the enzymology sense, but in general a substance binding instead of the conjugate, and competing with it for binding on the protein studied, the "binder") is left to bind together to the studied protein. From the ratio of bound and unbound conjugate, the bond strength can then be determined. Analogously, if the conjugate is immobilized on adsorbed streptavidin and the studied protein binds to it, it is again possible to add potential "inhibitor" sample to the studied protein and thus test whether the "inhibitor" interferes with binding the protein to the conjugate.

Immunoprecipitation (or "pull-down", i.e. an analogous method using substances other than antibodies) involves a polymeric conjugate binding to a solid phase, e.g. streptavidin sepharose. After washing away the unbound conjugate, the resin with bound conjugate is incubated with a sample containing the protein recognized by the conjugate. After incubation, the resin is washed and the protein is released from the resin (by heating in the presence of SDS, changing the pH, changing the ionic strength, etc.). Alternatively, the polymeric conjugate can be added directly to the sample and the resulting protein-conjugate complexes are separated from the sample by addition of streptavidin sepharose.

Immunocytochemistry involves visualizing the proteins, the cell structures and cells by (confocal) fluorescence microscopy. The cells grown on a matrix suitable for microscopy are first incubated in the presence of a polymeric conjugate, and after washing away and eventual fixation of cells (formaldehyde) or cell nuclei staining (using DAPI or Hoechst) the coupled polymeric conjugate is visualized using fluorescence microscopy, preferably confocal microscopy.

Flow Cytometry allows the detection cell surface proteins; subsequently counting, sorting and separating the cells. Cells are first incubated in the presence of the polymeric conjugate and then the cells are suspended in a solution. The cell suspension is then passed through a capillary, which involves detection of the fluorescently labeled conjugates bound to the surface antigen. Based on the presence or absence of fluorescence on the cell surface (i.e. the presence or absence of surface antigen) cells can be separated from each other (i.e. FACS—fluorescence-activated cell sorting).

Measurement of surface plasmon resonance (SPR) is a biophysical technique to analyze the binding process (and consequently the strength of this bond) of two interacting substances. In one arrangement, it allows the determination of dissociation constant for the protein-conjugate bond; in another, the polymeric conjugate can be used to immobilize the protein to the biosensor surface, and then analyze the bond between the given protein and another substance. In the first case, the protein is bound to the antibody immobilized on a gold biosensor chip and then the bond of the conjugate to the protein is analyzed. In the second case, the polymeric conjugate is first attached to neutravidin immobilized on the gold biosensor chip, then a particular protein bound to it and thereafter binding of the test substance to the protein is analyzed.

According to the present invention, conjugates can be provided that enable for example the targeting of glutamate carboxypeptidase II (GCPII), glutamate carboxypeptidase III (GCPIII), HIV-1 protease, aspartic proteases, carbonic anhydrase II (CA-II), carbonic anhydrase VII (CA-VII), carbonic anhydrase IX (CA-IX).

Glutamate carboxypeptidase II is a membrane metallopeptidase, expressed most of all in the central nervous system (involved there in degradation of the N-acetyl-L-aspartyl-glutamate neurotransmitter. cleaved free glutamate then causes glutamate excitotoxicity) and in prostate. Due to the increased expression in prostate cancer and neovasculatures of most solid tumors, GCPII has for several years been considered as target for therapeutic intervention (both for the visualization of tumors and for targeted drug delivery).

Field of application of the present invention is not only in scientific research, particularly in biochemistry and molecular biology, and methods employing antibodies, but also in diagnostics, in biochemical laboratories, in biochemical investigations and in specific separation of biologically active substances.

EXAMPLES OF CARRYING OUT THE INVENTION

I. Synthesis of Specific Inhibitors

Figure 1:
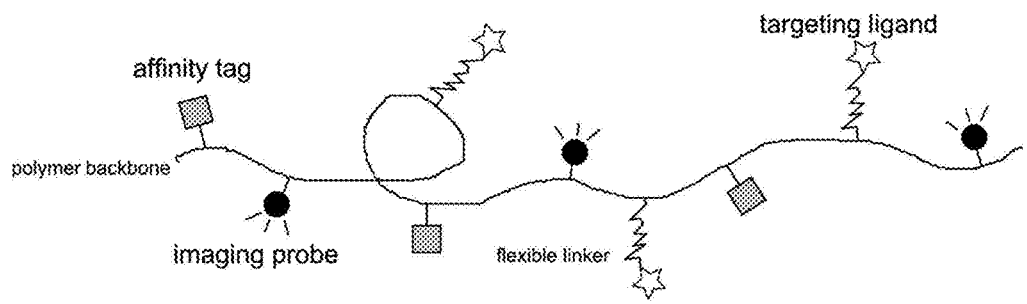
FIG. 1 shows a schematic structure of the polymeric conjugates.
Figure 2:
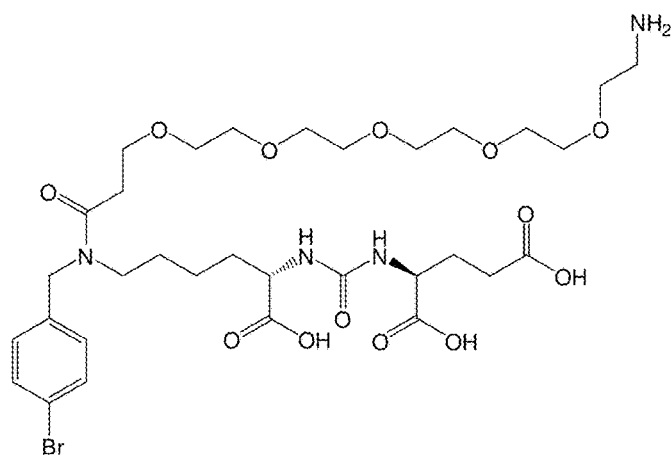
FIG. 2 shows the structure of the inhibitor intended for targeting of GCPII.
Figure 3:
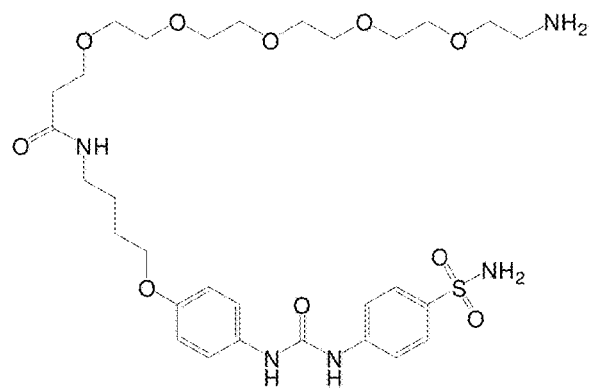
FIG. 3 shows the structure of the inhibitor intended for targeting of CA-IX.
Figure 4:
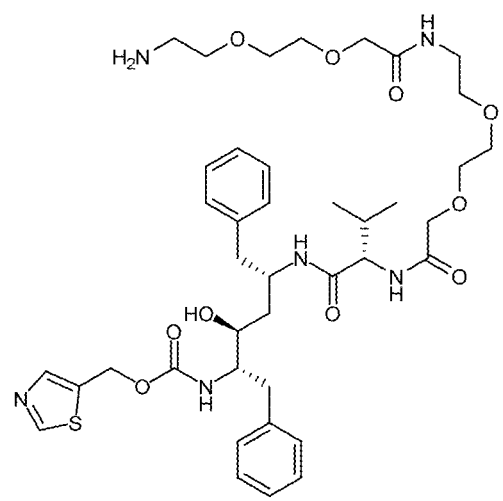
FIG. 4 shows the structure of the inhibitor intended for targeting of HIV-1 protease.
Figure 5:
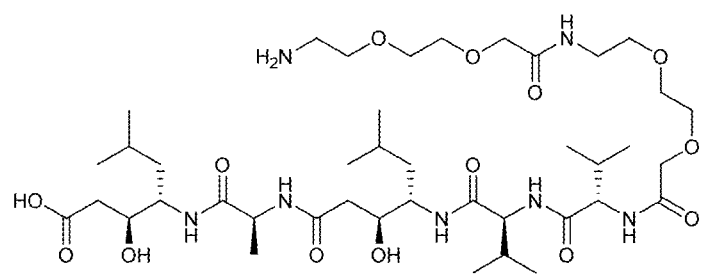
FIG. 5 shows the structure of the inhibitor intended for targeting of aspartic proteases.
Figure 6:
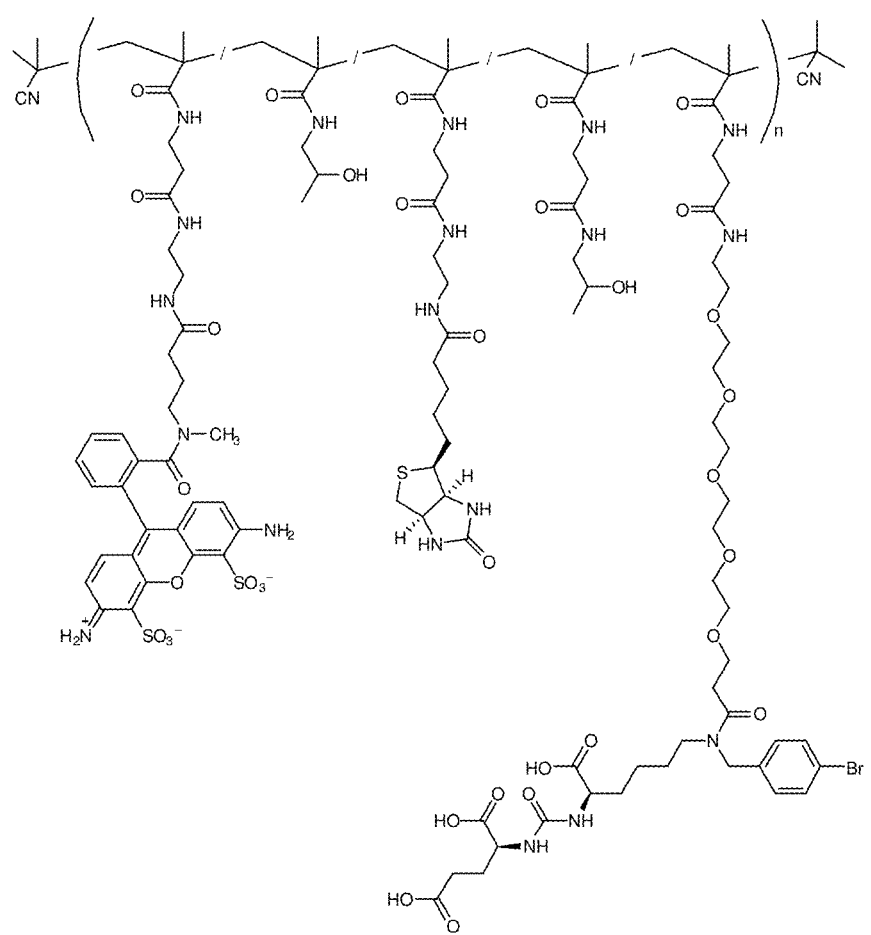
FIG. 6 shows the structure of Conjugate 1 intended for targeting of GCPII.
Figure 7:
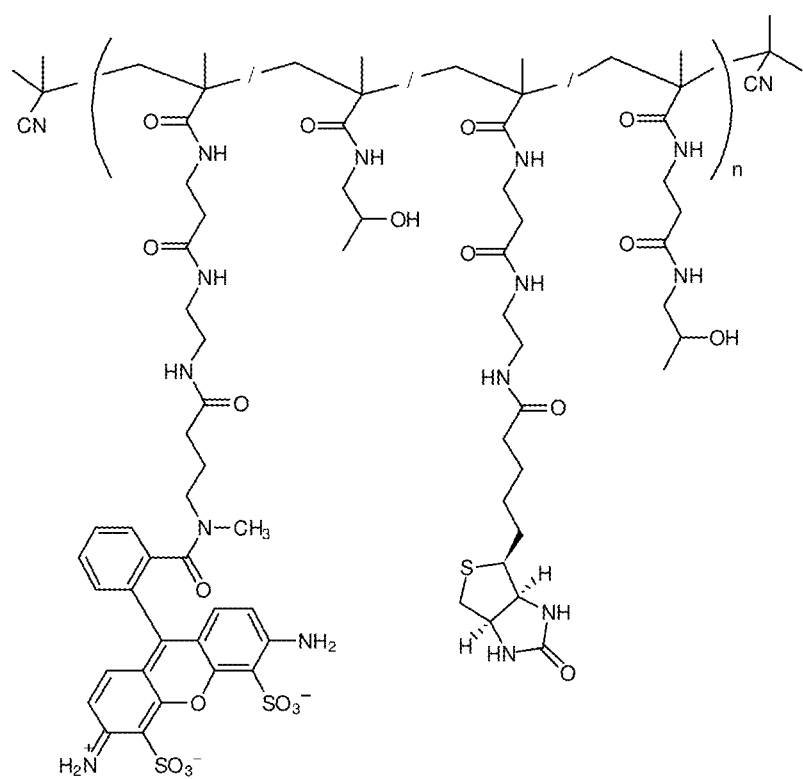
FIG. 7 shows the structure of comparative Conjugate 2 without inhibitor serving as a negative control.
Figure 8:
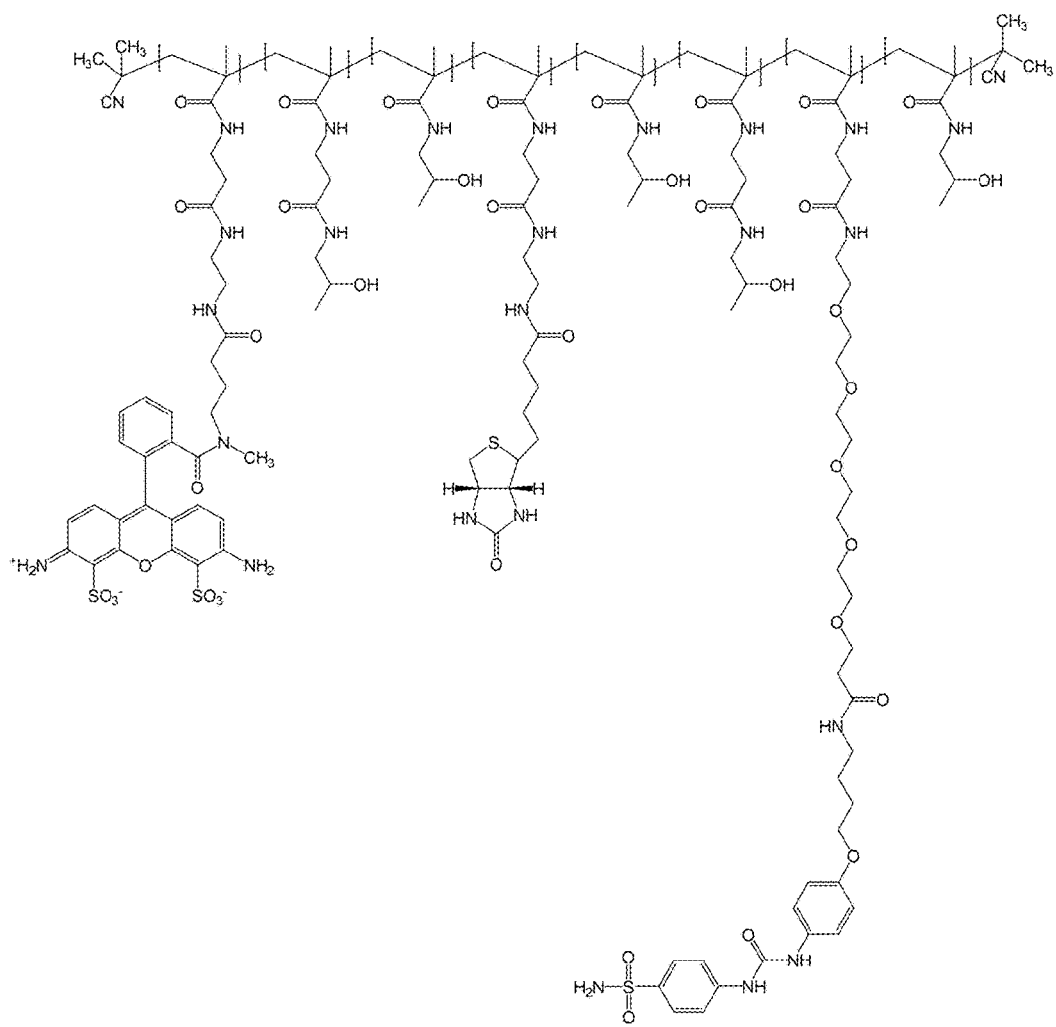
FIG. 8 shows the structure of Conjugate 3 intended for targeting of CA-IX.
Figure 9:
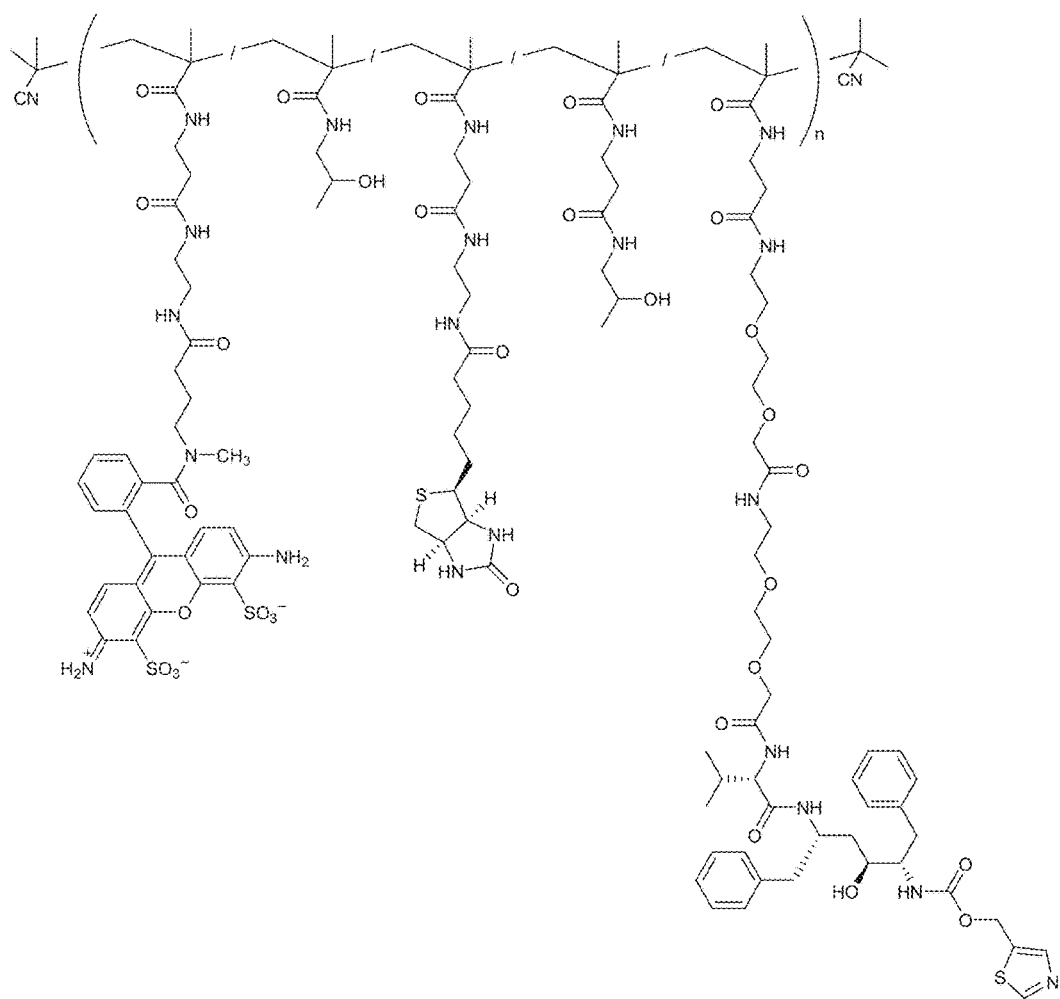
FIG. 9 shows the structure of Conjugate 4 intended for targeting of HIV-1 protease.
Figure 10:
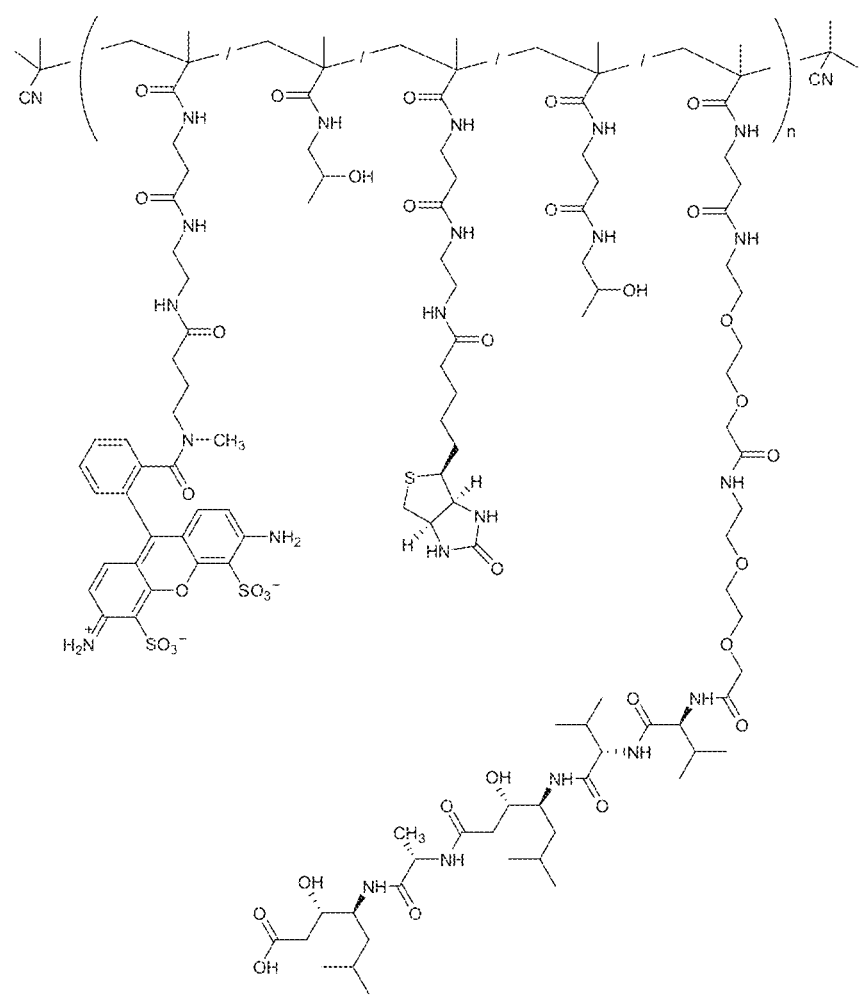
FIG. 10 shows the structure of Conjugate 5 intended for targeting of aspartic proteases.

All chemicals used were from Sigma-Aldrich unless stated otherwise. All inhibitors tested in biological assays were purified using Waters Delta 600 preparative HPLC system (flow rate 7 ml/min; gradient shown for each compound, including retention times), Waters SunFire C18 OBD Prep Column, 5 μm, 19×150 mm. Purity of compounds was checked on an analytical Jasco PU-1580 HPLC system (flow rate 1 ml/min with a constant gradient of 2-100% acetonitrile in 30 minutes; retention time is shown for each compound) with Watrex C18 Analytical Column, 5 μm, 250×5 mm. Final compounds were at least of 99% purity and their structure was further confirmed using HR-MS on LTQ Orbitrap XL (Thermo Fisher Scientific) and NMR (Bruker Avance I™ 500 MHz equipped with a cryo-probe). All interaction constants are given in Hz.

Example 1: Preparation of GCPII Inhibitor with a Linker (Compound A)

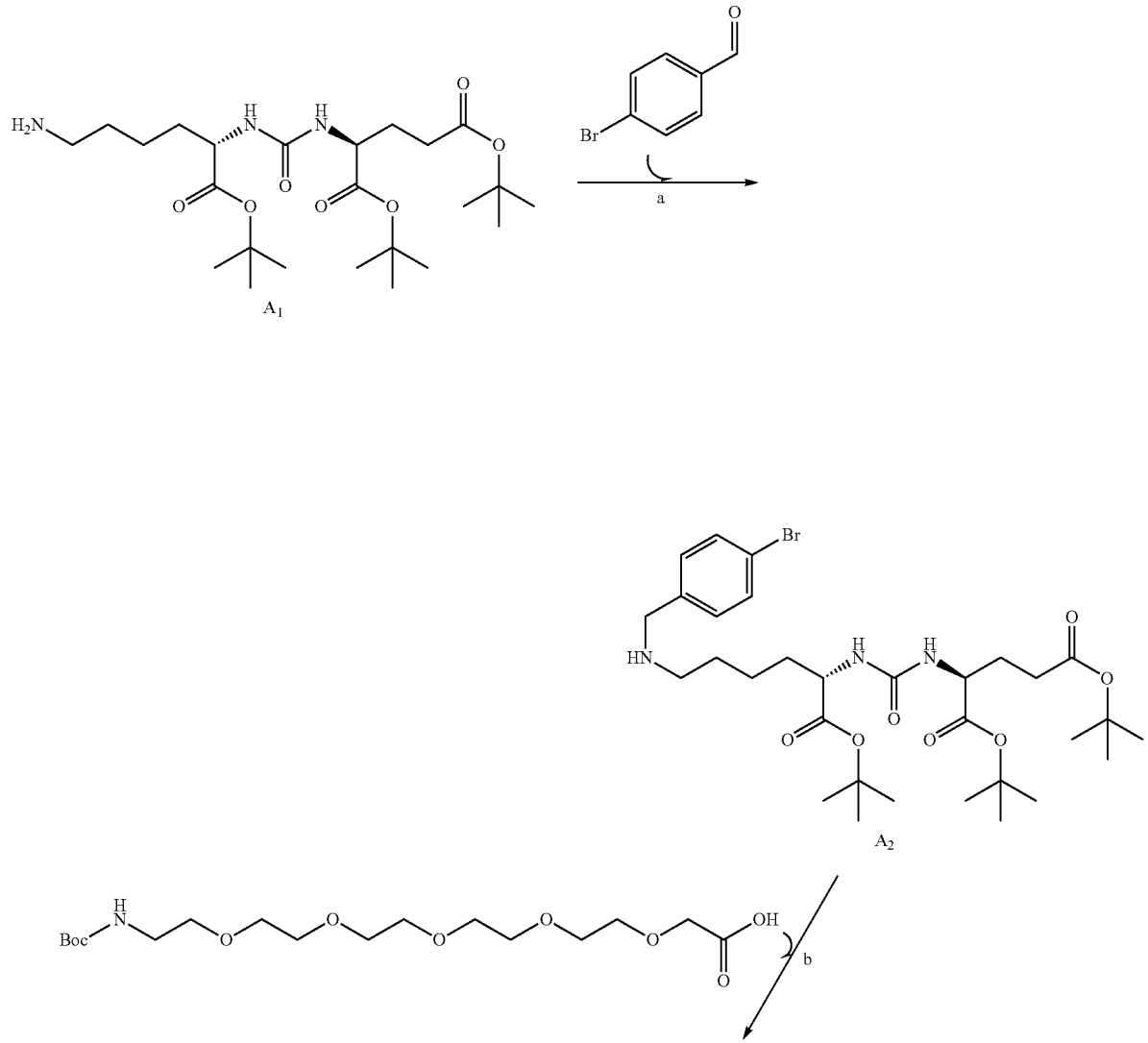

-continued

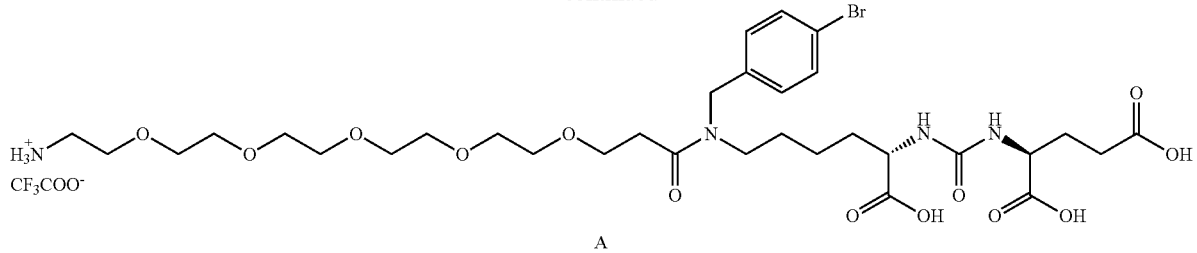

a) NaBH₃CN, MeOH + 1%AcOH;
b) 1) TBTU, DIEA, DMF; 2) TFA

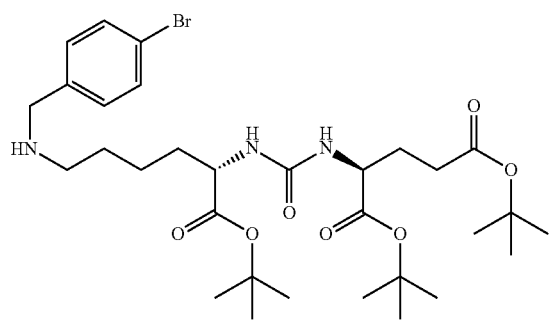 [SMILES: CC(C)(C)OC(=O)CC[C@H](NC(=O)N[C@@H](CCCCNCc1ccc(Br)cc1)C(=O)OC(C)(C)C)C(=O)OC(C)(C)C]

Di-tert-butyl 2-(3-(6-((4-bromobenzyl)amino)-1-(tert-butoxy)-1-oxohexan-2-yl)ureido)pentanedioate; Compound A₂

300 mg (0.615 mmol, 1 eq) di-tert-butyl 2-(3-(6-amino-1-(tert-butoxy)-1-oxohexan-2-yl)ureido)pentanedioate (Compound A₁, prepared according to [10]) and 120 mg (0,646 mmol, 1.05 eq) of 4-bromobenzaldehyde was dissolved in 5 ml methanol in a round-bottom flask. 50 µl of glacial acetic acid was added and, after rapid mixing, 120 mg (1.85 mmol, 3.0 eq) of sodium cyanoborohydride in one portion. After 12 hours, the reaction was stopped by adding 10 ml of water. After 10 minutes, the reaction mixture was further diluted with 50 ml of water and was extracted three times with ethyl acetate (3×25 ml). The organic phase was dried and evaporated and the raw product was purified by chromatography on silica gel (eluent: EtOAc+1% ammonia saturated in water, TLC analysis, Rf=0.55). The weight of the obtained pure product was 395 mg (yield=48%).

Analytical HPLC (gradient 2-100%. 30 min) RT=23.4 min. HR-MS (ESI+): counted for $C_{31}H_{51}O_7N_3Br$ [M]⁺ 656.29049. Found 656.29062. ¹H NMR (500 MHz; DMSO-d6): 7.47 (m; 2H; m-Ph); 7.27 (m; 2H; o-Ph); 6.29 (d; 1H; J=8.5; HN-Glu-2); 6.24 (d; 1H; J=8.4; HN-Lys-2); 4.02 (btd; 1H; =8.6; J²=5.1; Glu-2); 3.96 (td; 1H; J¹=8.1; J²=5.4; Lys-2); 3.62 (s; 2H; CH₂-Ph); 2.41 (t; 2H; J=7.1; Lys-6); 2.25 (ddd; 1H; J¹=16.6; J²=8.8; J³=6.8; Glu-4b); 2.18 (ddd; 1H; J¹=16.6; J²=8.8; J³=6.1; Glu-4a); 1.86 (m; 1H; Glu-3b); 1.66 (m; 1H; Glu-3a); 1.57 (m; 1H; Lys-3b); 1.49 (m; 1H; Lys-3a); 1.40 (m; 2H; Lys-5); 1.38 (bs; 27H; tBu); 1.29 (m; 2H; Lys-4). ¹³C NMR (125.7 MHz; DMSO-d6): 172.50 (Lys-1); 172.11 (Glu-1); 171.63 (Glu-5); 157.31 (NH—CO—NH); 140.83 (i-Ph); 131.07 (m-Ph); 130.26 (o-Ph); 119.52 (p-Ph); 80.76 (CH(CH₃)₃); 80.45 (CH(CH₃)₃); 79.95 (CH(CH₃)₃); 53.18 (Lys-2); 52.38 (CH₂-Ph); 52.36 (Glu-2); 48.49 (Lys-6); 32.17 (Lys-3); 31.07 (Glu-4); 29.24 (Lys-5); 27.93 (CH(CH₃)₃); 27.84 (CH(CH₃)₃); 27.82 (CH(CH₃)₃); 27.77 (GLu-3); 23.03 (Lys-4).

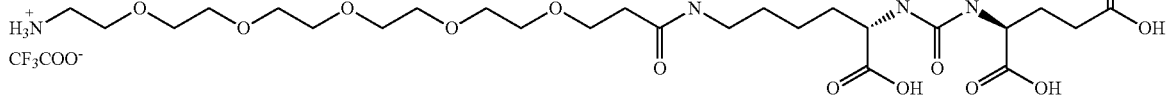

(24S,28S)-19-(4-bromobenzyl)-24,28,30-tricarboxy-18,26-dioxo-3,6,9,12,15-pentaoxa-19,25,27-triaza-triakontan-1-aminium 2,2,2-trifluoroacetate, Compound A 137 mg (0.34 mmol, 1.1 eq) BocNH-PEG₅-COOH (PurePEG, LLC) was dissolved in 1 ml DMF together with 1222 mg (0.38 mmol, 1.25 eq) of TBTU. 132 µl (0.76 mmol, 2.5 eq) of DIEA was then added all at once to the mixture, and the mixture was stirred for 10 min. 200 mg (0.30 mmol, 1 eq) of Compound A₂ dissolved in 1 ml DMF was then added to the mixture and the reaction was monitored by TLC until the Compound A₂ disappeared (about 4 hours). DMF was then removed using a rotary evaporator, the reaction mixture was dissolved in 20 ml of ethyl acetate and extracted twice with saturated solution of NaHCO₃, twice with 10% KHSO₄ and once with brine. The organic phase was dried and evaporated by rotary evaporation to dryness. Subsequently, 1 ml of TFA was added to the oily raw product and sonicated for 15 min. TFA was removed by a stream of nitrogen and the product was finally purified by preparative HPLC (gradient: 15-50% ACN, R_T=33 min). The weight of product obtained was 83.4 mg (yield of isolation was 30%).

Analytical HPLC (grad. 2-100%, 30 min): $R_T$=17.1 min. HR-MS (ESI−): Counted for $C_{32}H_{50}O_{13}N_4Br$ $[M]^-$ 777.25632. Found 777.25681.

Example 2: Synthesis of Inhibitor of Carbonic Anhydrase IX (Compound B)

Compound B was prepared according to the scheme below:

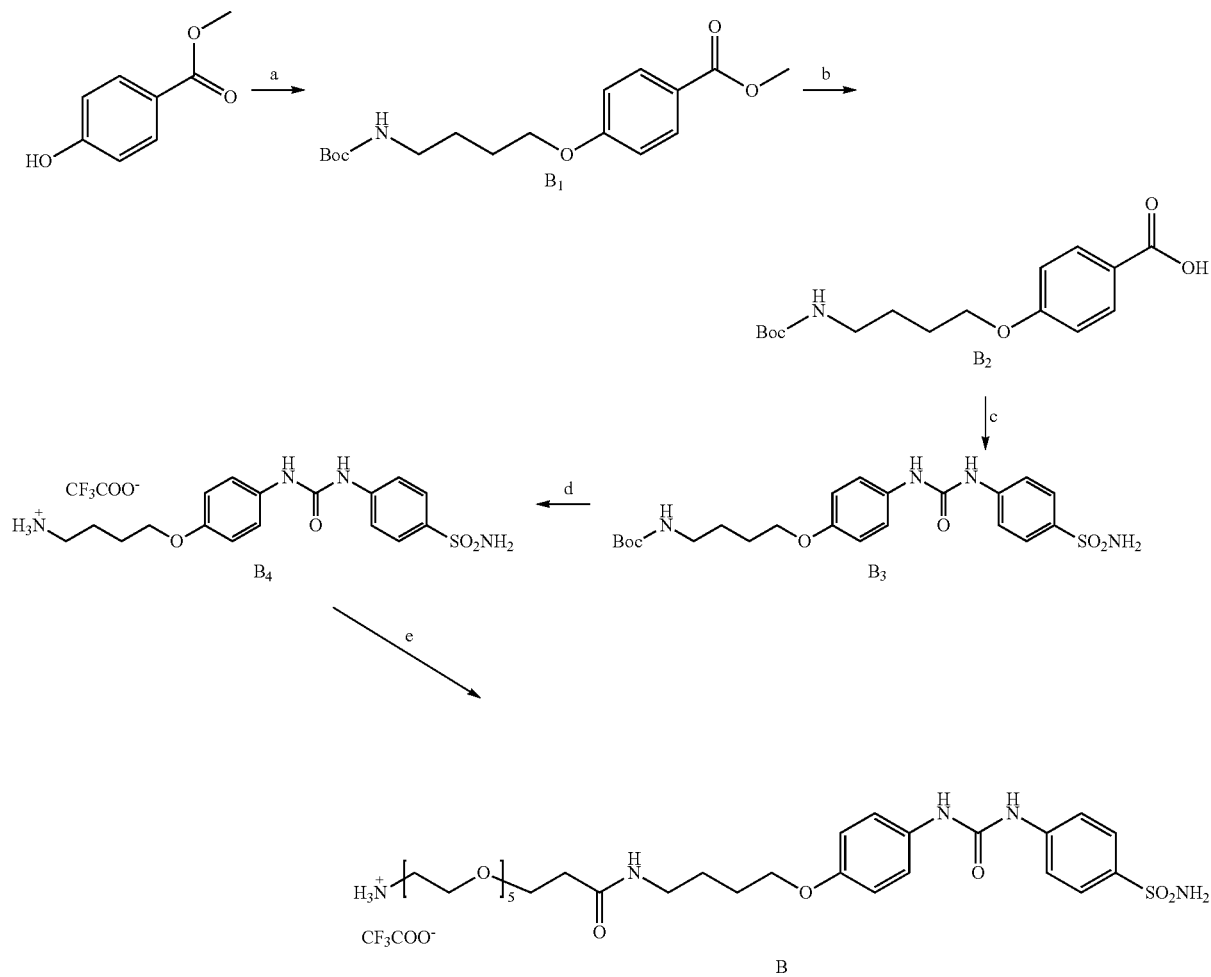

a) tert-butyl (4-hydroxybutyl)karbamát, (Ph)₃P, DIAD, THF;
b) 5M NaOH, MeOH/H₂O, reflux 6 hod;
c) 1) DPPA, DIEA, Tol, RT až 90° C.; 2) sulfanilamid, ACN, 60° C.;
d) TFA;
e) 1) Boc—PEG₅—COOH, TBTU, DIEA, DMF; 2) TFA methyl 4-(4-((tert-butoxycarbonyl)amino)butoxy)benzoate, Compound $B_1$ 161 mg (1 eq, 1.06 mmol) of methyl 4-hydroxybenzoate, 300 mg (1.5 eq, 1.59 mmol) of tert-butyl (4-hydroxybutyl) carbamate and and 400 mg (1.5 eq, 1.59 mmol) of triphenylphosphine was mixed in 10 ml of THF. 312 µl (1.5 eq, 1.59 mmol) of DIAD was then added all at once to the solution and the reaction was stirred overnight. The reaction mixture was then evaporated and the raw product was purified by column chromatography (He:EtOAc 4:1, RF=0.25). The weight of the obtained white powder was 260 mg, representing a 75% yield.

Note: the methyl 4-hydroxybenzoate had the same RF as the product, so 1.5 eq was used with other compounds.

MS (ESI+): counted for $C_{17}H_{25}O_5N$ $[MNa]^+$ 346.17. Found 346.2. $^1H$ NMR (400 MHz; CDCl₃) δ 7.95 (d; J=8.9 Hz; 2H); 6.87 (d; J=8.9 Hz; 2H); 4.71 (s; 1H); 3.99 (t; J. 6.2 Hz; 2H); 3.85 (s; 3H); 3.17 (dd; J=12.8; 6.3 Hz; 2H); 1.86-1.75 (m; 2H); 1.69-1.61 (m; 2H); 1.42 (s; 9H). $^{13}C$ NMR (101 MHz; CDCl₃) δ 166.92 (s); 162.78 (s); 156.10

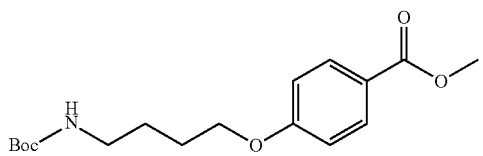 [SMILES: COC(=O)c1ccc(OCCCCNC(=O)OC(C)(C)C)cc1]

(s); 131.64 (s); 122.57 (s); 114.12 (s); 79.20 (s); 67.73 (s); 51.89 (s); 40.29 (s); 28.49 (s); 26.86 (s); 26.49 (s).

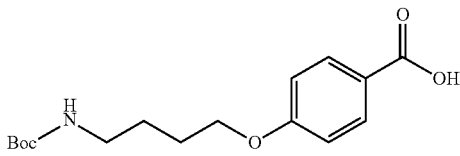 [SMILES: CC(C)(C)OC(=O)NCCCCOc1ccc(C(=O)O)cc1]

4-(4-((tert-butoxycarbonyl)amino)butoxy)benzoic Acid, Compound B$_2$ 270 mg of Compound B$_1$ was dissolved in 5 ml methanol and 5 ml of 5 M NaOH was then added to the solution. The mixture was refluxed until TLC analysis showed total disappearance of Compound B$_1$ (6 hours). The reaction mixture was diluted with 20 ml EtOAc, the aqueous phase was acidified with 10% KHSO$_4$ to acidic pH and extracted twice with 20 ml of EtOAc. This gave 240 mg of an oily product which, after removal of residual solvent, changed to white crystalline solid. Total yield was 95%.

HR-MS (ESI-): counted for C$_{16}$H$_{22}$O$_5$N [M]$^-$ 308.16. Found 308.2. $^1$H NMR (400 MHz; CDCl$_3$) δ 8.03 (d; J=8.9 Hz; 2H); 6.91 (d; J=9.0 Hz; 2H); 4.65 (s; 1H); 4.04 (t; J=6.2 Hz; 2H); 3.27-3.20 (m; 2H); 1.91-1.78 (m; 2H); 1.69 (dd; J=14.8; 7.2 Hz; 2H); 1.44 (s; 9H). $^{13}$C NMR (101 MHz; CDCl$_3$) δ 171.51 (s); 163.46 (s); 156.20 (s); 132.42 (s); 121.92 (s); 114.28 (s); 79.42 (s); 67.86 (s); 40.36 (s); 28.56 (s); 26.89 (s); 26.53 (s).

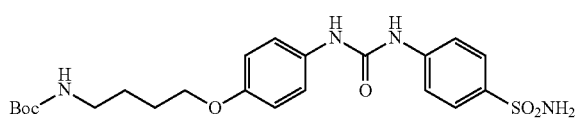

tert-butyl (4-(4-(3-(4-sulfamoylphenyl)ureido)phenoxy)butyl)carbamate, Compound B$_3$ 720 mg (1 eq, 2.33 mmol) of Compound B$_2$ was dissolved in 15 ml of anhydrous toluene followed by addition of 810 μl of DIEA (2 eq, 4.65 mmol). 552 μl of DPPA (1.1 eq, 2.56 mmol) was added all at once to the reaction mixture and the temperature of the mixture was increased to 90° C. for 2 hours. The reaction mixture was then evaporated and dissolved in anhydrous ACN. 601 mg (1.5 eq, 3.49 mmol) of sulphanilamide was then added all at once to the mixture and the temperature was increased to 60° C. for 15 hours. All volatiles were evaporated after 12 hours and the raw product was purified by column chromatography (He:EtOAc, 2:5, RF=0.25). The weight of product obtained was 340 mg, representing a 30% yield.

MS (ESI+): counted for C$_{22}$H$_{30}$O$_6$N$_4$S [MNa]$^+$ 501.17. Found 501.2. $^1$H NMR (400 MHz; DMSO) δ 8.98 (s; 1H); 8.59 (s; 1H); 7.71 (d; J=8.8 Hz; 2H); 7.59 (d; J=8.9 Hz; 2H); 7.34 (d; J=9.0 Hz; 2H); 7.20 (s; 2H); 6.91-6.81 (m; 3H); 3.91 (t; J=6.4 Hz; 2H); 2.96 (dd; J=12.9; 6.7 Hz; 2H); 1.71-1.61 (m; 2H); 1.51 (dt; J=13.1; 6.5 Hz; 2H); 1.37 (s; 9H). $^{13}$C NMR (101 MHz; DMSO) δ 155.37 (s); 154.02 (s); 152.16 (s); 142.99 (s); 136.40 (s); 132.04 (s); 126.61 (s); 120.14 (s); 117.12 (s); 114.50 (s); 77.06 (s); 67.05 (s); 40.35 (overlap with solvent peak) 27.77 (s); 26.85 (s); 25.73 (s).

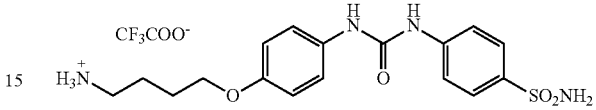

18-oxo-23-(4-(3-(4-sulfamoylphenyl)uredio)phenoxy-3,6,9,12,15-pentaoxa-19-azatrikosan-1-aminium 2,2,2-trifluoroacetate, Compound B$_4$ 500 mg Compound B$_3$ was dissolved in 1 ml of TFA and alternately sonicated and stirred for 15 min. TFA was then removed with nitrogen gas, and the product without further purification and characterization was used in the next step.

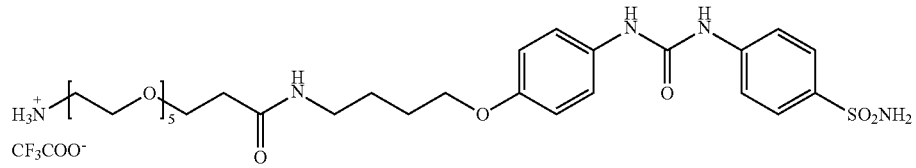

18-oxo-23-(4-(3-(4-sulfamoylphenyl)ureido)phenoxy)-3,6,9,12,15-pentaoxa-19-azatrikosan-1-aminium 2,2,2-trifluoroacetate, Compound B 46 mg (1 eq, 112 μmol) BocNH-PEG$_5$-COOH (PurePEG, LLC) was dissolved in 0.5 ml of DMF along with 36 mg (1 eq, 112 μmol) of TBTU and 49 μl (2.5 eq, 279 μmol) of DIEA. 55 mg (1 eq, 112 μmol) of Compound B$_4$ was added to this solution and the mixture was stirred overnight. The solvent was then evaporated and the raw product was dissolved in 10 ml of EtOAc. The organic phase was extracted twice with saturated NaHCO$_3$, twice with 10% KHSO$_4$, dried and evaporated. 53 mg of product was isolated, to which 1 ml of TFA was added and the mixture was alternately sonicated and stirred for 15 minutes. TFA was then removed with nitrogen gas, and the product was purified by preparative HPLC (gradient 10-50% ACN in 40 min, RT=22 min). The weight of product obtained was 17 mg, representing a 31% yield.

Analytical HPLC: RT=16.5 min. HR-MS (ESI): calculated for C$_{30}$H$_{48}$O$_{10}$N$_5$S [MH]$^+$ 670.31164. Found 670.31164.

Example 3: Preparation of HIV-1 Protease Inhibitor with a Linker (Compound C)

Compound C, based on a commercially available HIV protease inhibitor drug ritonavir (RTV), was synthesized according to the below depicted scheme:

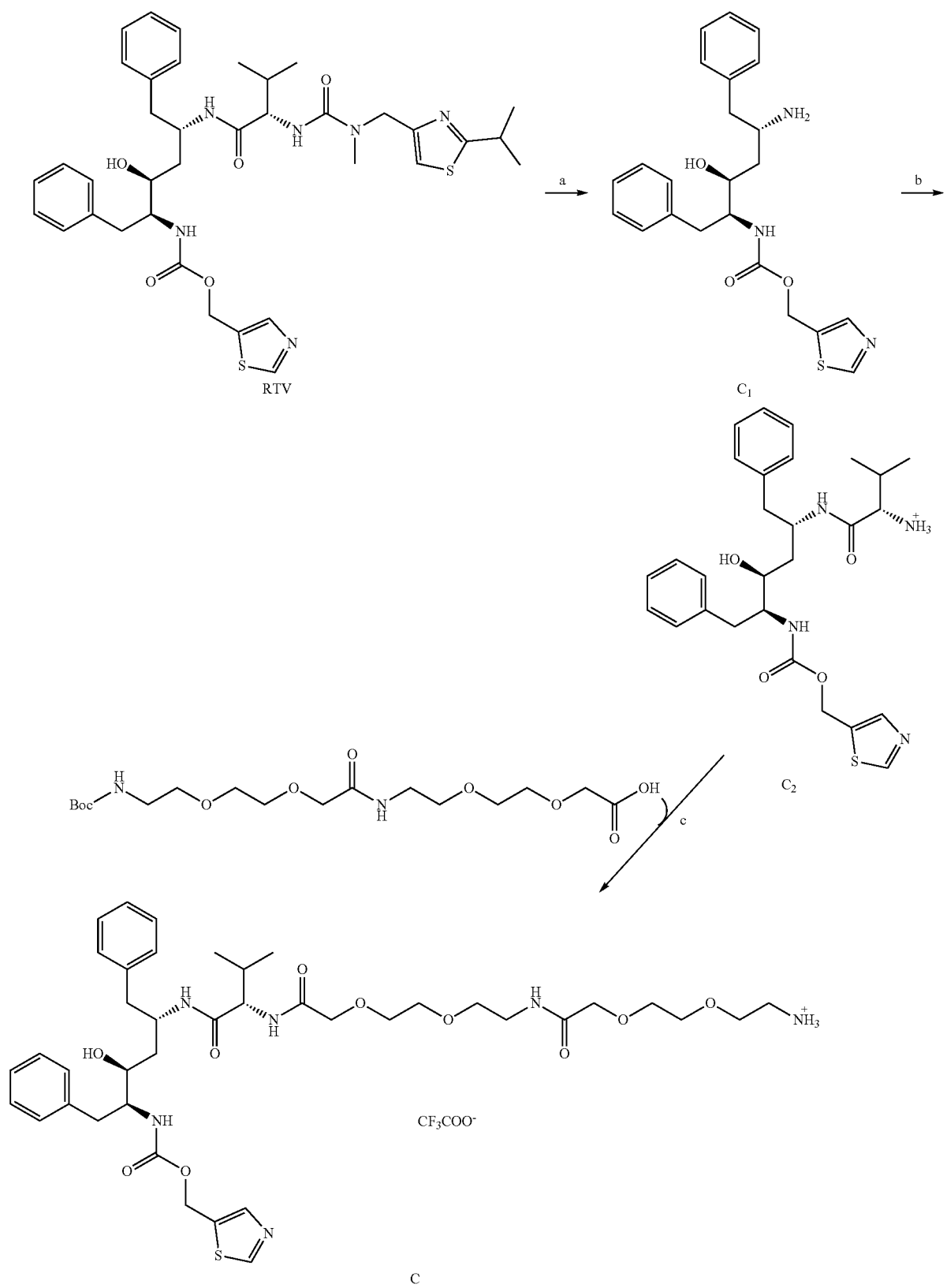
a) 1) Dioxane/HCl, 65° C., 20 h 2) K₂CO₃;
b) 1) Boc—Val—OH, TBTU, DIEA, DMF, 2) TFA;
c) 1) TBTU, DIEA, DMF, 2) TFA.

Isolation of ritonavir (RTV) from commercially available capsules: RTV is suspended in capsules in an oily mixture of rather non-polar compounds. 50 tablets (100 mg RTV each) were cut open and the oily substance was squeezed out into a round-bottom shaped 2 l flask. 200 ml of hexan was added along with 500 ml of diethyl ether. The resulting suspension was triturated and sonicated for 3 hours until all oil turned into a white precipitate. This precipitate was filtered and again triturated/sonicated in pure diethyl ether, after which the pure RTV was filtered. 3.6 g of RTV was obtained (isolation yield 72%). The purity of RTV was determined by HPLC and was well above 99% (analytical HPLC RT=23.7 min).

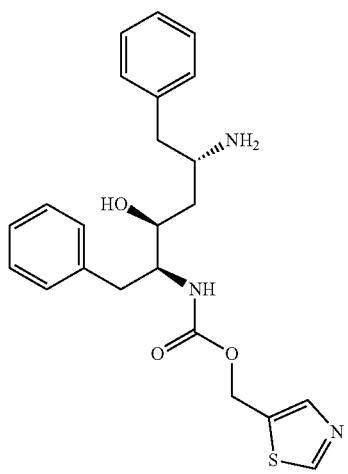 [SMILES: N[C@@H](Cc1ccccc1)C[C@H](O)[C@H](Cc1ccccc1)NC(=O)OCc1cncs1]

Partial Hydrolysis of Ritonavir (RTV), thiazol-5-ylmethyl ((2S,3S,5S)-5-amino-3-hydroxy-1,6-diphenylhexan-2-yl)carbamate, Compound $C_1$ 1.00 g of RTV was dissolved in 50 ml of dioxan in a bottom-round flask. 50 ml of concentrated hydrochloric acid was added and the resulting mixture was stirred at 65° C. for 20 hours (note that different temperature and/or time lead to different cleavage products). After 20 hours the mixture was let cool down to RT. The reaction mixture was neutralized by addition of $K_2CO_3$ until the resulting mixture showed basic pH. The solvents were concentrated using rotary evaporater to roughly 50 ml and diluted by 150 ml of water and washed 3 times by 100 ml of EtOAc. The water phase was discarded and organic phase was dried and evaporated. 885 mg of crude product was obtained and was used in the next step without further purification (purity roughly 70%—HPLC determination). For spectral determination, 50 mg was purified using preparative HPLC (gradient: 20-50% ACN in 40 minutes. $R_T$=15 min). Analytical HPLC $R_T$=17.3 min. HRMS (ESI+): calculated for $C_{23}H_{28}O_3N_3S$ [M]+ 426.18459. Found 426.18454. NMR measured for trifluoroacetate salt. $^1$H NMR (500 MHz, DMSO-d6): 9.06 (d, 1H, $^4J$=0.8, N—CH—S), 7.84 (q, 1H, $^4J$=0.8, S—C—CH—N), 7.81 (bs, 3H, $NH_3^+$), 7.32-7.15 (m, 10H, Ph-), 7.20 (bs, 1H, NH), 5.50 (bs, 1H, OH), 5.15 (dd, 1H, $J_{gem}$=13.2, $^4J$=0.8, O—$CH_2$), 5.11 (dd, 1H, $J_{gem}$=13.2, $^4J$=0.8, COO—$CH_2$), 3.69 (m, 1H, HO—CH), 3.67 (m, 1H, HO—CH—CH—NH), 3.50 (bm, 1H, $NH_3^+$—CH), 2.87 (dd, 1H, $J_{gem}$=14.0, $^3J$=6.4, $NH_3$+—CH—$CH_2$-Ph), 2.80 (dd, 1H, $J_{gem}$=14.0, $^3J$=7.3, $NH_3^+$—CH—$CH_2$-Ph), 2.79 (dd, 1H, $J_{gem}$=13.7, $^3J$=3.7, NH—CH—$CH_2$-Ph), 2.79 (dd, 1H, $J_{gem}$=13.7, $^3J$=10.5, NH—CH—$CH_2$-Ph), 1.58 (bs, 2H, OH—CH—$CH_2$—CH). $^{13}$C NMR (125.7 MHz, DMSO-d6): 155.39 (O—C—N), 155.77 (N—CH—S), 143.23 (S—C—CH—N), 139.52 (Ph), 136.37 (Ph), 134.14 (S—C—CH—N), 129.61 (Ph), 129.18 (Ph), 128.81 (Ph), 128.23 (Ph), 127.07 (Ph), 126.12 (Ph), 69.81 (HO—CH), 57.49 (COO—$CH_2$), 56.94 (HO—CH—CH—NH), 50.87 ($NH_3^+$—CH), 38.71 ($NH_3^+$—CH—$CH_2$-Ph), 35.69 (NH—CH—$CH_2$-Ph), 34.66 (CH—$CH_2$—CH).

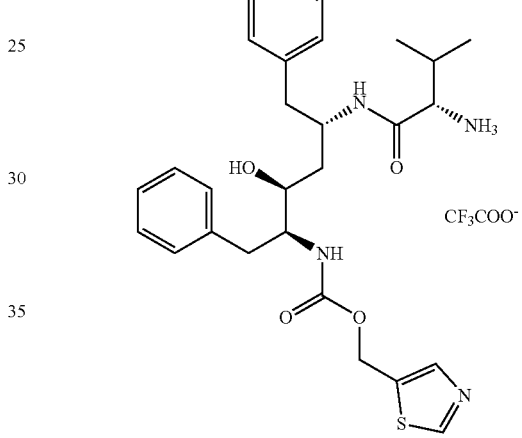

Thiazol-5-ylmethyl ((2S,3S,5S)-5-((S)-2-amino-3-methylbutanamido)-3-hydroxy-1,6-diphenylhexan-2-yl)carbamate, Compound $C_2$ 526 mg (1.64 mmol, 1.0 eq) of TBTU was added to 690 µl of DIEA (3.94 mmol, 2.4 eq). The crude hydrolysate of RTV (700 mg, 1.64 mmol, 1.0 eq), dissolved in 1 ml of DMF, was added after 5 minutes of stirring in one portion. The reaction was left overnight and DMF was rotary evaporated. The reaction mixture was dissolved in 50 ml of EtOAc and washed two times by saturated $NaHCO_3$, two times with 10% $KHSO_4$ and once with brine. The organic mixture was dried, evaporated and the product was purified using Flash chromatography (TLC analysis: EtOAc, $R_f$=0.65). Product was further dissolved in 5 ml of hot EtOAc and 5 ml of diethyl ether was added. The resulting gel was filtrated and dried to give very pure (>99%, HPLC) 250 mg of product (yield=25%). The product was then treated with TFA (approx. 1 ml) for 15 minutes, alternately sonicated and stirred. The remaining TFA was then removed by flow of nitrogen. The oily product was dissolved in water/ACN and was lyophilisated. Analytical HPLC $R_T$=17.4 min. HRMS (ESI+): calculated for $C_{28}H_{37}O_4N_4S$ [M]$^+$ 525.25300. Found 525.25292. $^1$H NMR (500 MHz, DMSO-d6): 9.06 (d, 1H, $^4$J=0.8, N—CH—S), 8.24 (d, 1H J=8.2, —NH—CO), 8.00 (bd, 3H, J=5.2, —NH$_3{}^+$), 7.85 (q, 1H, $^4$J=0.8, S—C—CH—N), 7.28-7.13 (m, 10H, Ph–), 6.94 (d, J=9.4, 1H, NH—CO—O), 5.12 (d, 2H, $^4$J=0.8, O—CH$_2$), 4.16 (m, 1H, CH—NH—CO), 3.78 (m, 1H, CH—NH$_3{}^+$, partial overlap with water residual peak), 3.58 (td, 1H, J=6.8, J=2.0, CH—OH), 3.48 (m, 1H, Ph-CH$_2$—CH—NH), 2.72-2.67 (m, 4H, 2×CH—CH$_2$-Ph), 2.00 (m, 1H, CH—(CH$_3$)$_2$), 1.50 (m, 1H, OH—CH—CH$_2$), 1.43 (m, 1H, OH—CH—CH$_2$), 0.89 (d, 3H, J=6.8 —CH$_3$), 0.84 (d, 3H, J=6.8 —CH$_3$). $^{13}$C NMR (125.7 MHz, DMSO-d6): 167.33 (CO Val), 158.33 (q, $J_{C,F}$=34.4, CF$_3$COO—), 155.79 (O—C—N), 155.71 (N—CH—S), 143.23 (S—C—CH—N), 139.50 (Ph), 138.55 (Ph), 134.23 (S—C—CH—N), 129.56 (Ph), 129.17 (Ph), 128.30 (Ph), 128.25 (Ph), 126.26 (Ph), 126.09 (Ph), 116.44 (q, $J_{C,F}$=294.8, CF$_3$—COO$^-$) 68.90 (HO—CH), 57.56 (CO—CH—NH3), 57.44 (COO—CH$_2$), 55.74 (HO—CH—CH—NH), 47.98 (CONH—CH), 39.75 (NH—CH—CH$_2$-Ph), 37.77 (—CH$_2$—CH—CH—), 37.33 (Ph-CH$_2$—CH—NH), 30.04 (CH(CH$_3$)$_2$), 17.26 and 18.69 (2×CH$_3$).

group was then removed by stirring in 1 ml of TFA for 15 minutes. The product was purified using preparative HPLC (gradient: 15-50% ACN in 40 minutes. R$_T$=31 min). Analytical HPLC R$_T$=17.7 min. HRMS (ESI+): calculated for $C_{40}H_{59}O_{10}N_6S$ [M]$^+$ 815.40079. Found 815.40096. $^1$H NMR (500 MHz, DMSO-d6): 9.05 (d, 1H, J=0.8, N—CH—S), 7.96 (d, 1H, J=8.7, NH—CO-Val), 7.85 (q, 1H, J=0.8, S—C—CH—N), 7.81 (vbs, 3H, —NH$_3{}^+$), 7.79 (bt, 1H, J=5.8, Linker NH—CO), 7.31 (d, 1H, J=NH-Val-2), 7.24-7.08 (m, 10H, 2×Ph), 6.92 (d, 1H, J=9.4, NH—COO—CH$_2$-thiazol), 5.16 (dd, 1H, J$_{gem}$=13.2, $^4$J=0.8, NH—COO—CH$_2$-thiazol), 5.12 (dd, 1H, J$_{gem}$=13.2, $^4$J=0.8, NH—COO—CH$_2$-thiazol), 4.13 (m, 1H, CH—NH—CO-Val), 4.13 (dd, 1H, $^2$J=9.3, $^3$J=6.8, Val-2), 3.92-3.89 (m, 4H, linker 2×NH—CO—CH$_2$—), 3.82 (m, 1H, CH—NH—COO—CH$_2$-thiazol), 3.62-3.51 (m, 12H, linker, OH—CH), 3.46 (bt, 2H, O—CH$_2$—CH$_2$—NH—CO—CH$_2$—), 3.29 (bt, 2H, O—CH$_2$—CH$_2$—NH—CO—CH$_2$—), 2.98 (m, 2H, CH$_2$—NH$_3{}^+$), 2.71-2.65 (m, 2H Ph-CH$_2$—CH—NH-Thiazol, 1H Ph-CH$_2$—NH-Val), 2.58 (dd, 1H, J$_{gem}$=13.6, $^3$J=8.4, Ph-CH$_2$—NH-Val), 1.84 (o, 1H, J=6.8, Val-3), 1.46 (m, 2H, OH—CH—CH$_2$—), 0.76 (d, 3H, J=6.8, Val-4), 0.74

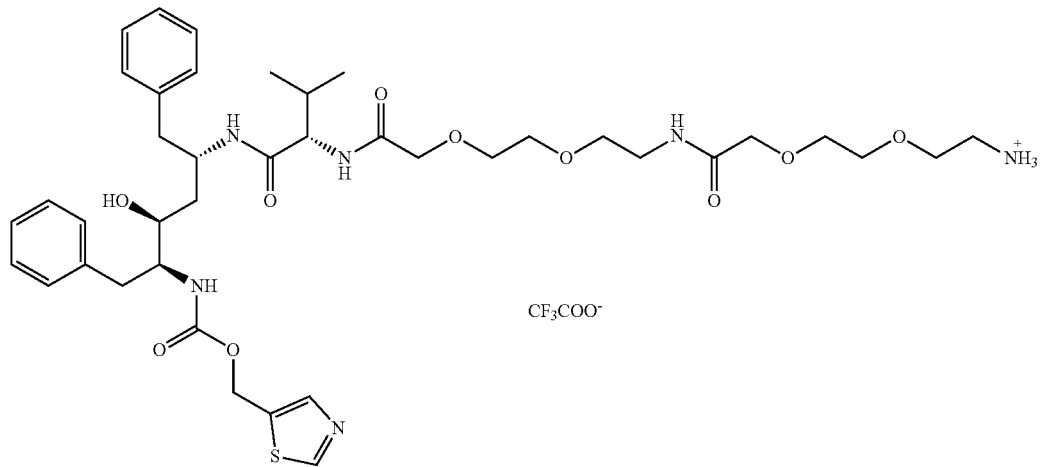 [SMILES: CC(C)[C@H](NC(=O)COCCOCCNC(=O)COCCOCCN)C(=O)N[C@@H](Cc1ccccc1)C[C@H](O)[C@H](Cc1ccccc1)NC(=O)OCc1cncs1 ; "CF3COO-"]

(5S,6S,8S,11S)-5,8-dibenzyl-6-hydroxy-11-isopropyl-3,10,13,22-tetraoxo-1-(thiazol-5-yl)-2,15,18,24,27-pentaoxa-4,9,12,21-tetraazanonacosan-29-aminium 2,2,2-trifluoroacetate, Compound C 64 mg (157 µmol, 1.0 eq) of Boc-O2Oc-O2Oc-OH (Iris-Biotech, #BAA1485) was dissolved in 1 ml of DMF along with 51 mg (157 µmol, 1.0 eq) of TBTU and 95 µl (558 µmol, 3.5 eq) of DIEA and the whole reaction mixture was stirred for 15 minutes. 100 mg (157 µmol, 1.0 eq) of compound C$_2$ (dissolved in 0.5 ml of DMF) was added into the mixture in one portion. After 3 hours all volatiles were evaporated, the crude product was dissolved in 25 ml of EtOAc and was washed two times with saturated NaHCO$_3$, two times with 10% KHSO$_4$ and once with brine. The organic layer was dried and evaporated. The Boc-protecting (d, 3H, J=6.8, Val-4). $^{13}$C NMR (125.7 MHz, DMSO-d6): 170.04 (Val-1), 169.56 (NH—CO-Linker), 168.90 (Val-NH—CO—), 158.31 (q, J=34.4, CF$_3$COO$^-$), 155.82 (COO—CH2-thiazol, S—CH—N), 143.24 (S—C—CH—N), 139.60 (i-Ph), 138.92 (i-Ph), 134.30 (S—C—CH—N), 129.47 (o-Ph), 129.25 (o-Ph), 128.20 (m-Ph), 128.08 (m-Ph), 126.04 (p-Ph), 126.03 (p-Ph), 116.46 (q, J=293.5, CF$_3$COO$^-$), 70.44 (linker), 70.17 (linker), 70.03 (linker), 69.83 (linker), 69.66 (linker), 69.48 (linker), 69.22 (linker), 69.11 (CH—OH), 66.85 (linker), 57.40 (O—CH$_2$-thiazol), 57.07 (Val-2), 55.64 (CH—COO—CH$_2$-thiazol), 47.45 (CH—NH-Val), 39.90 (CH$_2$—CH—NH-Val), 38.74 (CH$_2$—NH$_3{}^+$), 38.44 (OH—CH—CH$_2$), 38.23 (CH$_2$—NH—COO—CH$_2$), 37.41 (OCO—NH—CH$_2$-Ph), 31.19 (Val-3), 19.48 (Val-4), 18.10 (Val-4).

Example 4: Preparation of Aspartic Proteases Inhibitor with a Linker (Compound D)

The structure of the inhibitor is based on pepstatin A, an inhibitor of aspartic proteases.

D

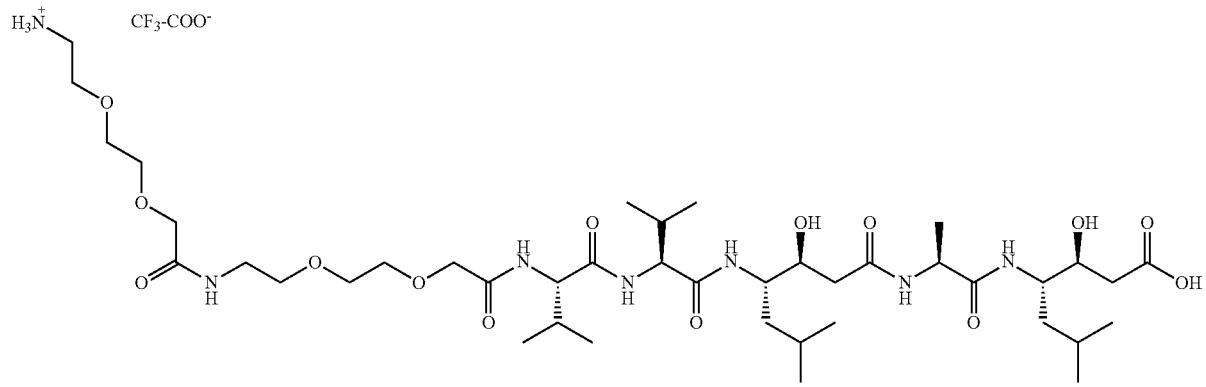

(19S,22S,25S,26S,30S,33S)-33-((S)-2-carboxy-1-hydroxyethyl)-26-hydroxy-25-isobutyl-19,22-diisopropyl-30,35-dimethyl-8,17,20,23,28,31-hexaoxo-3,6,12,15-tetraoxa-9,18,21,24,29,32-hexaazahexatriacontan-1-aminium, Compound D, NH$_2$-amidoPEG-pepstatin The pepstatin inhibitor was synthesized by standard amino-Fmoc synthesis on solid phase, using 2-chlortrityl chloride resin (Iris-Biotech). The first amino acid (Fmoc-Sta-OH) was attached to the solid phase according to the manufacturer's instructions: the resin was left to react with Fmoc-Sta-OH (0.6 eq to resin substitution) in presence of 4 equivalents of DIEA for 2 hours in DCM. The remaining reactive residues were quenched with mixture of DCM/MeOH/DIEA (17:2:1) for 15 minutes. All other amino acids and the linker Boc-O2Oc-O2Oc-OH (Iris-Biotech, #BAA1485) were added using HOBt/DIC method. The peptide was then cleaved from the solid phase using 95% TFA and the crude product was purified using preparative HPLC (gradient: 10-50% ACN in 40 minutes. $R_T$=26 min). Analytical HPLC $R_T$=16.5 min. HRMS (ESI−): calculated for $C_{41}H_{76}O_{14}N_2$ [M]⁻ 890.54557. Found 890.54413.

II. Synthesis of HPMA Copolymers and their Conjugates

Example 5: Synthesis of a Conjugate of HPMA Copolymer with a GCPII Inhibitor (Compound A), an ATTO488 Fluorophore and Biotin (Conjugate 1)

Synthesis of Polymeric Precursor Poly(HPMA-Co-Ma-β-Ala-TT)

Monomeric compounds N-(2-hydroxypropyl)methacrylamide (HPMA) and 3-(3-methacrylamido-propanoyl)thiazolidine-2-thione (Ma-β-Ala-TT) were prepared according to published procedure [3, 7]. The polymeric precursor poly(HPMA-co-MA-β-Ala-TT) was prepared using RAFT-copolymerization (reversible addition-fragmentation chain-transfer). 500 mg of HPMA was dissolved in 3.8 ml of tert-butanol (85 mol %); 159 mg of MA-β-Ala-TT (15 mol %) dissolved in 0.8 ml of DMSO, 1.21 mg of 2-cyano-2-propylbenzodithioate and 0.45 mg of 2,2'-azobis(2-methylpropionitrile) were added to the solution and the solution was transferred into a polymerization vial. The mixture was purged with argon for 10 min and then the vial was sealed.

The polymerization reaction was performed at 70° C. for 16 h. The polymeric precursor was isolated by precipitation into acetone:diethylether (3:1), filtered, washed with acetone and diethyl ether and dried in vacuum. Dithiobenzoate end groups were removed according to a previously published procedure [11]. This procedure resulted in polymeric precursor poly(HPMA-co-MA-β-Ala-TT) with a molecular weight of $M_w$=85,900 g/mol, with polydispersity of D=1.22 and containing 13.4 mol % of reactive thiazolidine-2-thione groups.

Synthesis of Conjugate 1

The polymeric precursor poly(HPMA-co-Ma-β-Ala-TT) (0.045 g, $M_w$=85900 g/mol, 13.4 mol % TT), Compound A (6.2 mg) and N-(2-aminoethyl)biotinamide hydrobromide (biotin-NH$_2$) (5 mg) were dissolved in 0.2 ml of DMSO. ATTO488-NH$_2$ (2.5 mg) was dissolved in 0.1 ml of DMSO and added to the solution of polymeric precursor. N,N-diisopropylethylamine (DIPEA) (2.5 µl) was then added and the reaction mixture was stirred for 4 hours at room temperature, then 1-amino-propan-2-ol (5 µl) was added to the solution and the reaction mixture was stirred for 10 min. The polymeric conjugate poly(HPMA-co-MA-β-Ala-CompoundA-co-MA-β-Ala-ATTO488-co-MA-β-Ala-NH-biotin) was then isolated by precipitation into acetone:diethyl ether (3:1), filtered, washed with acetone and diethyl ether and dried in vacuum. Polymeric conjugate was purified from low-molecular impurities by column chromatography on Sephadex LH-20 in methanol, precipitated in diethyl ether, filtered and dried in vacuum. The yield of the poly(HPMA-co-Ma-β-Ala-CompoundA-co-Ma-β-Ala-ATTO488-co-Ma-β-Ala-NH-biotin) conjugate was 33 mg, the content of inhibitor (Compound A) was 9.8%, the content of ATTO488 was 3.9% and biotin content was 9.8%.

Example 6: Synthesis of Comparative Conjugate of HPMA Copolymer with the ATTO488 Fluorophore and Biotin (Conjugate 2)

The polymeric precursor poly(HPMA-co-MA-β-Ala-TT) (0.045 g, Mw=85,900 g/mol, 13.4 mol % TT; see Example 5) and 5 mg of biotin-NH$_2$ were dissolved in 0.2 ml of DMSO. ATTO488-NH$_2$ (2.5 mg) was dissolved in 0.1 ml of DMSO and added to the solution of polymeric precursor. N,N-diisopropylethylamine (DIPEA) (2.5 µl) was then added, the reaction mixture was stirred for 4 hours at room temperature, 1-amino-propan-2-ol (5 µl) was added to the solution and the reaction mixture was stirred for 10 min. The polymeric conjugate poly(HPMA-co-Ma-β-Ala-ATTO488-co-Ma-β-Ala-NH-biotin) was then isolated by precipitation into acetone:diethyl ether (3:1), filtered, washed with acetone and diethyl ether and dried in vacuum. Polymeric conjugate was purified by column chromatography on Sephadex LH-20 in methanol, precipitated in diethyl ether, filtered and dried in vacuum. The yield of the poly(HPMA-co-Ma-β-Ala-ATTO488-co-Ma-β-Ala-NH-biotin) conjugate was 32 mg, ATTO488 content was 5.1% and biotin content 10.8%.

Example 7: Synthesis of a Conjugate of HPMA Copolymer with a CA-IX Inhibitor (Compound B), the ATTO488 Fluorophore and Biotin (Conjugate 3)

The polymeric precursor poly(HPMA-co-MA-β-Ala-TT) (0.045 g, M$_w$=85,900 g/mol, 13.4 mol % TT; see Example 5), Compound B (6.2 mg) and N-(2-aminoethyl) biotinamido hydrobromide (biotin-NH$_2$) (5 mg) and ATTO488-NH$_2$ (2.5 mg) were dissolved in 0.3 ml of DMSO. N,N-diisopropylethylamine (DIPEA) (8 µl) was added and the reaction mixture was stirred for 4 hours at room temperature; subsequently, 1-amino-propan-2-ol (5 µl) was added to the solution of and the reaction mixture was stirred for 10 min. The polymeric conjugate poly(HPMA-co-MA-β-Ala-CompoundB-co-MA-β-Ala-ATTO488-co-MA-β-Ala-NH-biotin) was then isolated by precipitation into acetone:diethyl ether (3:1), filtered, washed with acetone and diethyl ether and dried in vacuum. Polymeric conjugate was purified from low-molecular impurities by column chromatography on Sephadex LH-20 in methanol, precipitated in diethyl ether, filtered and dried in vacuum. The yield of the poly(HPMA-co-MA-β-Ala-CompoundB-co-MA-β-Ala-ATTO488-co-MA-β-Ala-NH-biotin) conjugate was 39 mg, the content of inhibitor (Compound B) was 10.5%, content of ATTO488 3.7% and content of biotin 8.6%.

III. Evaluation of Properties of Polymer Conjugates Using Biochemical Methods

Example 8: Inhibition of the GCPII Activity by Inhibitors and Conjugate 1

Inhibitory potency of the inhibitors and polymeric conjugates on the hydrolytic activity of GCPII were tested by HPLC (described in [12]) using a recombinant extracellular GCPII (Avi-GCPII; prepared according to [13]). 210 pg of GCPII was mixed with a solution of 25 mM Bis-Tris propane, 150 mM NaCl, pH 7.4, 0.001% monododecyl (oktaethylenglycol)ether (Affymetrix, Octaethylene glycol monododecyl ether) and inhibitor solution to a total volume of 180 µl in a 96-well plate. Ten different inhibitor concentrations covering the whole inhibition curve were used. Reactions were first incubated 5 min at 37° C., then initiated by addition of 20 µl of pteroyl-bis(L-glutamate) to a final concentration of 400 nM and incubated at 37° C. for 20 min. Reactions were stopped with 20 µl of 25 µM 2-(phosphonomethyl)pentanedioic acid (2-PMPA). Subsequently, 100 µl of the reaction mixture was analyzed in Agilent 1200 Infinity (Agilent Technologies, Inc.) on an RP-HPLC column Waters Acquity UPLC HSS T3 1.8 µm, 2.1×100 mm (Waters). HPLC analysis was performed isocratically in 2.7% acetonitrile and 97.3% 20 mM phosphate, pH 6.0. Substrate and product absorbance was measured at 281 nm. IC$_{50}$ values were obtained from GraFit v.5.0.11 (Erithacus Software Ltd.).

Kinetic parameters Avi-GCPII (K$_M$ and k$_{cat}$) for pteroyl-bis(L-glutamate) in reaction buffer used for determination of IC$_{50}$ were obtained by the procedure above, but without addition of inhibitor and with substrate concentrations between 15 nM and 400 nM (substrate conversion was of 13±2% in all reactions). Assuming competitive type of inhibition and using the values of K$_M$ and k$_{cat}$, the K$_i$ values for each inhibitor were determined from the Cheng-Prusoff equation [14].

Several inhibitors of GCPII were prepared and tested; they were based on the structure of glutamate-urea-lysine-linker and varied in different types of the linker [12]. Compound A was selected for conjugation to HPMA polymer, but all inhibitors tested reached nanomolar or subnanomolar K$_i$ values, and after their conjugation to HPMA copolymer, K$_i$ values (of the resulting polymeric conjugate) decreased by about 2-3 orders of magnitude (only Conjugate 1 containing Compound A selected and shown here). This decrease depended on the inhibitor and the amount of attached molecules of inhibitor. Besides these conjugates, a comparative conjugate without GCPII inhibitor (Conjugate 2) was also prepared as a negative control; this conjugate did not inhibit the activity of GCPII. K$_i$ values and the basic characteristics of the prepared compounds are given in Table 1.

TABLE 1

Prepared inhibitors and polymeric conjugates and their inhibition constants (K$_i$) for GCPII

| Compound designation | M$_r$ g/mol | Targeted towards | Number of inhibitors | K$_i$ [pM] | Modifications |
|---|---|---|---|---|---|
| 2-PMPA | 226 | GCPII | — | 370 ± 30 | — |
| Compound A | 780 | GCPII | — | 2,033 ± 426 | — |
| Conjugate 1 | 107,000 | GCPII | 13.7 | 3.1 ± 0.5 | Compound A, ATTO488, biotin |
| Conjugate 2 | 96,000 | — | 0 | N/A | ATTO488, biotin |

Example 9: Affinity Isolation ("Pull-Down") of GCPII Using Polymeric Conjugates and Subsequent Detection of GCPII by Western Blot LNCaP cells (cultured in 100 mm Petri dish) derived from cells of metastatic prostate adenocarcinoma and endogenously expressing GCPII were lysed by sonication in a water bath (3 min/0° C.) in 450 µl of 50 mM Tris-HCl, 150 mM NaCl, pH 7.4, 1% Tween 20. The resulting cell lysate was further diluted in 20 mM Tris-HCl, 150 mM NaCl, 0.1% Tween 20, pH 7.4 (TBST) to a final protein concentration of 200 µg/ml (concentration of GCPII was approximately 100 ng/ml). Meanwhile, the Conjugate 1 and Comparative Conjugate 2 (negative control showing nonspecific binding) were pre-bound to 20 µl Streptavidin Sepharose (5 µM solution in 200 µl TBST, 1 hour, 6° C.), and after washing twice with 200 µl TBST, the resin was mixed with 200 µl of LNCaP cell lysate and incubated at 6° C. for 12 h. The resin was then washed with 2×200 µl of TBST and subsequently, proteins were eluted by addition of 50 µl of sampled buffer for SDS-PAGE and by heating to 98° C. for 10 min.

To compare the efficiency of GCPII isolation using Conjugate 1, GCPII was isolated at the same time using 2G7 antibody [15] (ie. immunoprecipitation). The experiment was performed analogously to the experiment with polymeric conjugates: 5 µg of the antibody was pre-bound to 20 µl of Protein G Sepharose and the procedure followed as described above. Resin Protein G Sepharose without the antibody was used as negative control.

After isolation, samples were separated by SDS-PAGE electrophoresis and the gel was either stained with silver or blotted to a nitrocellulose membrane (semi-dry blotting: 15V/15 min). After transfer of proteins to the membrane, surface of the membrane was blocked with 0.55% (w/v) solution of casein in PBS (Casein Buffer 20×-4× Concentrate, SDT) at room temperature for 1 hour. Then, the blots were incubated with primary antibody GCP-04 [9] for 12 hours at 6° C. (200 ng/ml diluted in 0.55% solution of casein); then the blots were washed three times with PBS containing 0.05% Tween 20 (PBST) and incubated with a secondary goat antibody against mouse immunoglobulins conjugated to horseradish peroxidase(Thermo Scientific, diluted in 0.55% casein solution 1:25000). Finally, the blots were washed three times with PBST, and chemiluminescent substrate SuperSignal West Dura/Femto Chemiluminescent Substrate (Thermo Scientific) was applied on the membrane. Chemiluminescence was recorded using ChemiDoc-It™ 600 Imaging System (UVP).

Figure 11A:
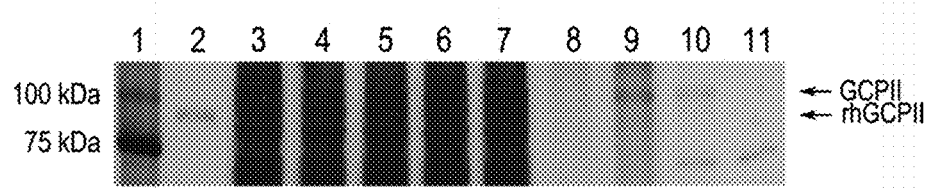
FIG. 11A shows the silver-stained gel demonstrating the affinity isolation of GCPII ("pull-down") from a lysate of LNCaP cells with Conjugate 1. Lane 1: All Blue Marker (0.5 µl); 2: rhGCPII standard (50 ng); 3: Lysate of LNCaP cells; 4: FT: Conjugate 2 (negative control); 5: FT: Conjugate 1; 6: FT: 2G7 antibody; 7: FT: negative control for 2G7 antibody; 8: Elution: Conjugate 2 (negative control); 9: Elution: Conjugate 1; 10: Elution: 2G7 antibody; 11: Elution: negative control for the 2G7 antibody. All lanes were loaded with 8 µl of the sample.
Figure 11B:
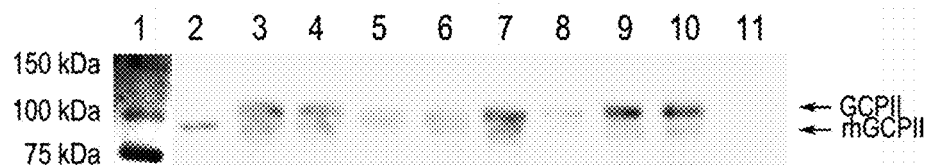
FIG. 11B shows a Western blot demonstrating the affinity isolation of GCPII ("pull-down") from a lysate of LNCaP cells with Conjugate 1. GCP-04 antibody [9] was used to visualize the GCPII. Lane 1: All Blue Marker (0.5 µl); 2: rhGCPII standard (5 ng); 3: lysate of LNCaP cells; 4: FT: Conjugate 2 (negative control); 5: FT: Conjugate 1; 6: FT: 2G7 antibody; 7: FT: negative control for 2G7 antibody; 8: Elution: Conjugate 2 (negative control); 9: Elution: Conjugate 1; 10: Elution: 2G7 antibody; 11: negative control for the 2G7 antibody. All lanes were loaded with 6 µl of the sample.

Conjugate 1 was able to affinity isolate GCPII from lysate of LNCaP cells endogenously expressing GCPII. The quantity of GCPII isolated with Conjugate 1 and with 2G7 antibody designed against native GCPII was practically the same (FIG. 11A, B). The advantage of polymeric conjugates against antibodies lies in the possibility of their use in cases where the use of antibodies is impossible or difficult, e.g. in immunoprecipitation of proteins from blood plasma, where large quantities of endogenous antibodies in blood compete with protein G for binding sites on the resin. Biotinylation of these antibodies may be a solution, which, however, may damage the antibody. Using biotinylated polymeric conjugates and a resin with streptavidin solves this problem, because endogenous antibodies are not biotinylated.

Example 10: Quantification of the Interaction of Polymeric Conjugates with GCPII Using Surface Plasmon Resonance (SPR)

All measurements of interaction of polymeric conjugates with relevant proteins using surface plasmon resonance (SPR) were conducted on a four-channel SPR sensor developed at the Institute of Photonics and Electronics AS CR in Prague [16-17]. In a typical experiment, the SPR chip (supplied by IPE ASCR) was immersed for 1 h at 37° C. in ethanol solution (7:3) of alkanethiols HS—$(CH_2)_{11}$-$PEG_4$-OH a HS—$(CH_2)_{11}$-$PEG_6$-O—$CH_2$—COOH (Prochimia) at a final concentration of 0.2 mM. The chip was subsequently rinsed with ethanol for UV spectroscopy, with deionized water and dried with nitrogen. Finally, the chip is attached to an SPR chip prism; all measurements were performed at 25° C. Activation of the terminal carboxyl groups on the sensor surface was carried out in situ by addition of a mixture (1:1) 11.51 mg/ml N-hydroxysuccinimide (NHS, Biacore), and 76.68 mg/ml 1-ethyl-3-(3-dimethylaminopropyl)-carbodiimide hydrochloride (EDC, Biacore) in deionized water for 5 min at a flow rate 20 µl/min. Following parts of the experiment were then conducted at a flow rate of 30 µl/min. Subsequently, a mixture of D2B antibody against native GCPII (20 ng/µl) with BSA (20 ng/µl) in 10 mM sodium acetate, pH 5.0, was applied for 8 minutes; the molar ratio D2B:BSA was 1:2.3. To remove non-specifically bound molecules, buffer of high ionic strength was used (PBS with 0.5 M NaCl), and then 1 M ethanolamine (Biacore) was applied for deactivation of the remaining activated carboxyl groups. Solution of recombinant extracellular GCPII (Avi-GCP II, prepared according to [13]) in 20 mM Tris-HCl, 150 mM NaCl, pH 7.4 (TBS) at a concentration of 8 ng/µl was used to immobilize the Avi-GCPII on the prepared gold chip coated with D2B antibody mixed with BSA. Finally a solution of the polymeric conjugate was injected (at a flow rate of 60 µl/min) in varying concentrations (association phase), followed by TBS only (dissociation phase).

Figure 12:
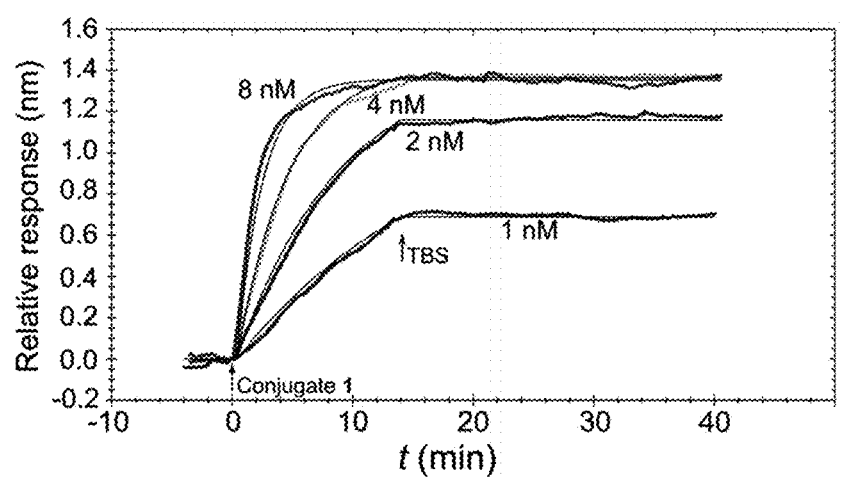
FIG. 12 shows a typical course of Conjugate 1 binding Avi-GCPII analyzed by SPR (surface plasmon resonance). Extracellular recombinant GCPII (Avi-GCPII) was immobilized on a gold chip coated with D2B antibody against native GCPII. Four different concentrations of Conjugate 1 were then applied to the prepared layer (a) 8 nM; b) 4 nM; c) 2 nM; d) 1 nM) and the association and dissociation phases of binding were monitored. Acquired curves were processed and then fitted in the TraceDrawer program v.1.5 (Ridgeview Instruments AB, Sweden).

Curves describing the bond were exported and analyzed in TraceDrawer v.1.5 (Ridgeview Instruments AB) to obtain the $k_{on}$ and $k_{off}$ parameters (FIG. 12).

Measurement of the kinetic parameters of bond between GCPII and Conjugate 1 revealed a high value of association rate of interaction ($k_{on}$=9.7·$10^5$ $M^{-1}s^{-1}$); the value of dissociation rate was below the detection limit of our SPR instrument ($k_{off}$<2·$10^{-5}$), and the exact value of the dissociation constant thus could not be determined ($K_D$<20 pM). This value is comparable to the best available antibodies against GCPII. Due to the very small value of $k_{off}$ there is practically no washing of GCPII bound to conjugate 1, which can be used for highly rigid immobilization of GCPII.

Example 11: ELISA for Quantification of GCPII Using Polymeric Conjugates

Sandwich ELISA, normally implemented with two antibodies, has been modified for the use of polymeric conjugates either for immobilisation or in the role of the second specific detection antibody. All steps of the experiment were performed at room temperature.

When using polymeric conjugates instead of immobilizing antibody, streptavidin (500 ng/well) in 100 mM borate buffer, pH 9.5, was sorbed (1 hour) to 96-well Maxisorb plates (Nunc). After washing with 3×200 µl of TBS, the uncovered surface of the well was blocked with 0.55% (w/v) solution of casein in TBS (Casein Buffer 20×-4× Concentrate, SDT, 24 hod). After further washing with 3×200 µl TBST, Conjugate 1 (100 nM in TBST) was bound to streptavidin (2 hours). The unbound polymer was washed off with 3×200 µl of TBST, and subsequently, solution of recombinant extracellular GCPII was added to the wells (rhGCPII; prepared according to [18]) in TBST (in amounts of 1 ng-1 pg/well, 20 min). After washing with 3×200 µl of TBST, specific murine antibody was added—J591 in TBST (25 ng/well, 1 h); after washing the antibody away with 3×200 µl of TBST, the secondary goat antibody was added that recognizes mouse IgG in TBST (100 ng/well, Thermo Scientific, 30 minutes). After washing with 5×200 µl of TBST, chemiluminescent substrate was added and luminescence was measured on a Tecan Infinite M1000 PRO spectrophotometric reader.

In the second case, the plate was first coated with 2G7 antibody in borate buffer (500 ng/well). After blocking the surface with casein and washing (see above) incubation with recombinant extracellular GCPII followed (rhGCPII; prepared according to [18]) in TBST (in amounts 1 ng-1 pg/well, 20 min). After washing with 3×200 µl of TBST, the solution of Conjugate 1 was added (at concentrations 0.5-1000 nM in TBST, 1 hour), subsequently washed away with 3×200 µl of TBST and NeutrAvidin conjugated to horseradish peroxidase (100 ng/well, Thermo Scientific) was added to the well. After washing with 5×200 µl of TBST, chemiluminescent substrate was added and luminescence was measured on a Tecan Infinite M1000 PRO spectrophotometric reader. With the classical ELISA method, two antibodies against native GCPII are used; limitation of this approach is the requirement of different epitopes of these two antibodies. E.g. two of the best known antibodies against GCPII—J591 and J415—can not be used together [19]. In the case of sandwich antibodies J591 and 2G7, this condition is met and the limit of detection is between 1-2 pg GCPII. In the first case, when the polymeric conjugate was first immobilized to streptavidin and then incubated with antigen (rhGCPII), the detection limit was approximately 30 pg. In the second case, when rhGCPII was first bound to the 2G7 antibody, and then the polymeric conjugate was added, the detection limit decreased to 0.5 pg of GCPII, i.e. lower value, as in the case of using the best sandwiches for GCPII quantification. An important advantage of polymers is their insensitivity to the presence of interfering antibodies, i.e. a frequent and serious cause of false positivity in the case of using two antibodies. Interfering antibodies recognize epitopes on antibodies and can couple the antibodies used in the sandwich without the presence of the determined antigen itself. Polymeric conjugates, as molecules of completely different chemical nature, do not cause such problems.

ELISA method was also used for the determination of $K_D$ values for the tested polymers. The $K_D$ value should correspond to the $K_i$ determined by measuring the inhibition of GCPII activity (see Tab. 1), or to the $K_D$ value determined by measuring this interaction using SPR. The $K_D$ value determined with the ELISA method, however, was approximately 40 times higher (for Conjugate 1, the $K_D$ value was 115 pM; the $K_i$ was 3.1 pM, and the $K_D$(SPR) <20 pM). The difference is probably caused by using different methods.

Example 12: Modified ELISA Method for Testing GCPII Inhibitors

ELISA method was also used to test the GCPII inhibitors; the procedure was analogous to Example 11. This method is based on the competition of Conjugate 1 and the tested potential GCPII inhibitor for binding into the active site of GCPII. The amount of bound Conjugate 1 is then determined by chemiluminescence and subsequently related to the sample without test inhibitor (see below).

The Maxisorp plate (Nunc) was first coated with 2G7 antibody in borate buffer (500 ng/well). After blocking the surface with casein and washing it away (see above), incubation with recombinant extracellular GCPII followed (rhGCPII; prepared according to [18]) in TBST (10 ng/well, 1 hr). After washing with 3×200 µl of TBST, either a solution containing either conjugate 1 alone was added (5 mM in TBST for 1 hour; reference sample), or a mixture of Conjugate 1 (5 mM in TBST) and the test substance in the selected concentration (typically 0.1-100 µM in TBST). After incubation for 1 h at room temperature, the wells were washed with 5×200 µl TBST. NeutrAvidin conjugated to horseradish peroxidase was then added to the wells (100 ng/well, Thermo Scientific), and after washing with 5×200 µl of TBST, chemiluminescent substrate was added and luminescence was measured on a Tecan Infinite M1000 PRO spectrophotometric reader.

Example 13: Flow Cytometry of LNCaP and PC3 Cells Using Polymeric Conjugates

Cell lines derived from prostate cancer cells (LNCaP and PC3) were cultured on 100 mm Petri dish until reaching 80% confluency. NCaP cells were cultured in complete RPMI-1640 medium (Sigma-Aldrich), while PC-3 cells in complete DMEM-High Glucose medium (GE Healthcare), containing L-glutamine (final concentration 4 mM) and FBS (final concentration 10%).

After reaching 80% confluence, the medium was removed, cells rinsed with PBS and incubated for 3 min in 1.5 ml of 0.25% trypsin and 0.01% EDTA. Cells were resuspended in this solution and transferred to 8 ml of DMEM or RPMI complete medium, centrifuged 250×g/2 min and washed with 5 ml PBS. Subsequently, 500 µl of 10% fetal bovine serum in PBS was added to block the cell surface (1 hr/37° C.). The amount of cells was counted using Countess® Automated Cell Counter (Invitrogen). 50 µl of cell suspension (containing $2 \times 10^5$ cells) were then incubated with 10 nM Conjugate 1 or Conjugate 2 (1 h/37° C.). Finally the cell suspension was diluted with 150 µl of PBS and the cell fluorescence was analyzed with BD LSR Fortessa™ flow cytometer. Analysis of the results was performed with BD FACSDiva™ Software.

Figure 13:
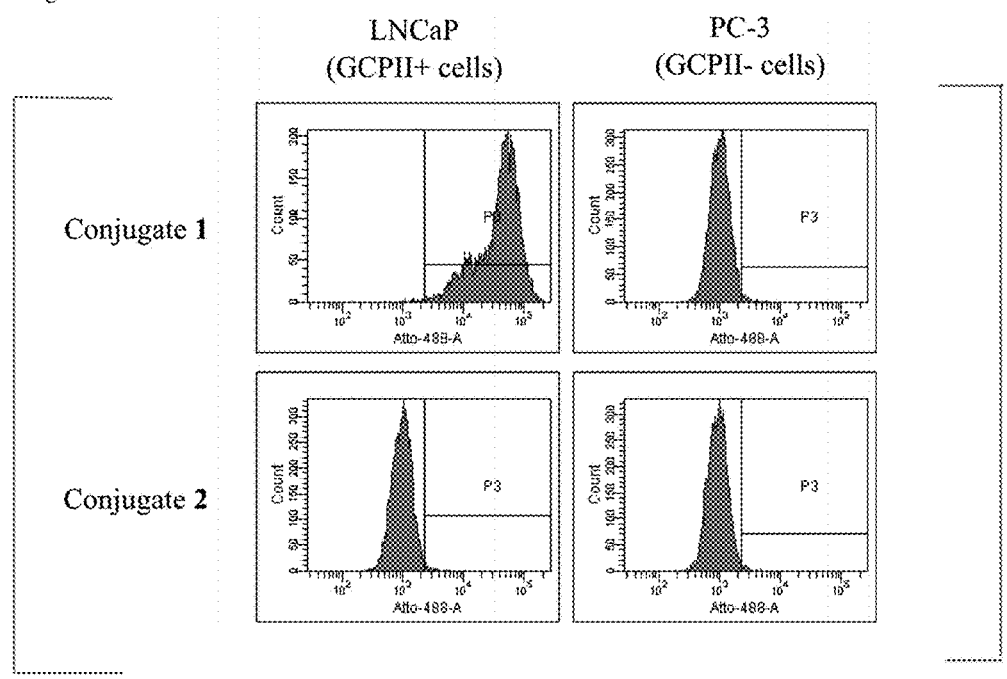
FIG. 13 shows flow cytometry of cells expressing GCPII (LNCaP) and not expressing GCPII (PC-3). Cells were incubated in the presence of 10 nM Conjugate 1 or Conjugate 2 and then analyzed on a Fortessa™ BD LSR cytometer.

As is evident from FIG. 13, fluorescence of LNCaP cells incubated with Conjugate 1 is significantly higher than in PC-3 cells non-expressing GCPII, suggesting specific binding to cells through interaction of GCPII on the cell surface and its inhibitor to Conjugate 1.

Example 14 Visualization of GCPII on the Cell Surface Using the Polymeric Conjugates (Immunocytochemistry)

Fluorescence visualization of GCPII on cell surface (immunocytochemistry) using polymeric conjugates was performed on two types of cell lines derived from prostate cancer: LNCaP cells (endogenously expressing GCPII) and PC-3 (non-expressing endogenous GCPII). Cells were cultured overnight in complete RPMI-1640 medium (LNCaP) or DMEM-High glucose medium (PC-3). A solution of Conjugate 1 or Conjugate 2 was added to the medium to a final concentration of 10 nM and the cells were incubated in their presence for 2 hours at 37° C. Subsequently, the medium was removed, cells rinsed with 0.5 ml PBS and incubated with 0.5 µg/ml solution of Hoechst Stain Solution H33258 (Sigma) for 15 minutes for staining cell nuclei. Finally, cells were rinsed with 0.5 ml PBS. Images were acquired with a Zeiss LSM 780 confocal laser microscope (Carl Zeiss, Inc., Oberkochen, Germany) with an oil immersion objective (Plan-Apochromat 63×/1.40 Oil DIC M27).

Microscope settings for individual channels were as follows: for Hoechst 33258: excitation 3% of the output of 405 nm diode laser (max. output 30 mW), emission spectral detector range: 410-585 nm; for ATTO488: excitation 3.5% output of 488 nm argon laser (max. output 25 mW), emission spectral detector range: 517-534 nm. Images were processed in ZEN 2011 software (Carl Zeiss Microscopy).

Figure 14:
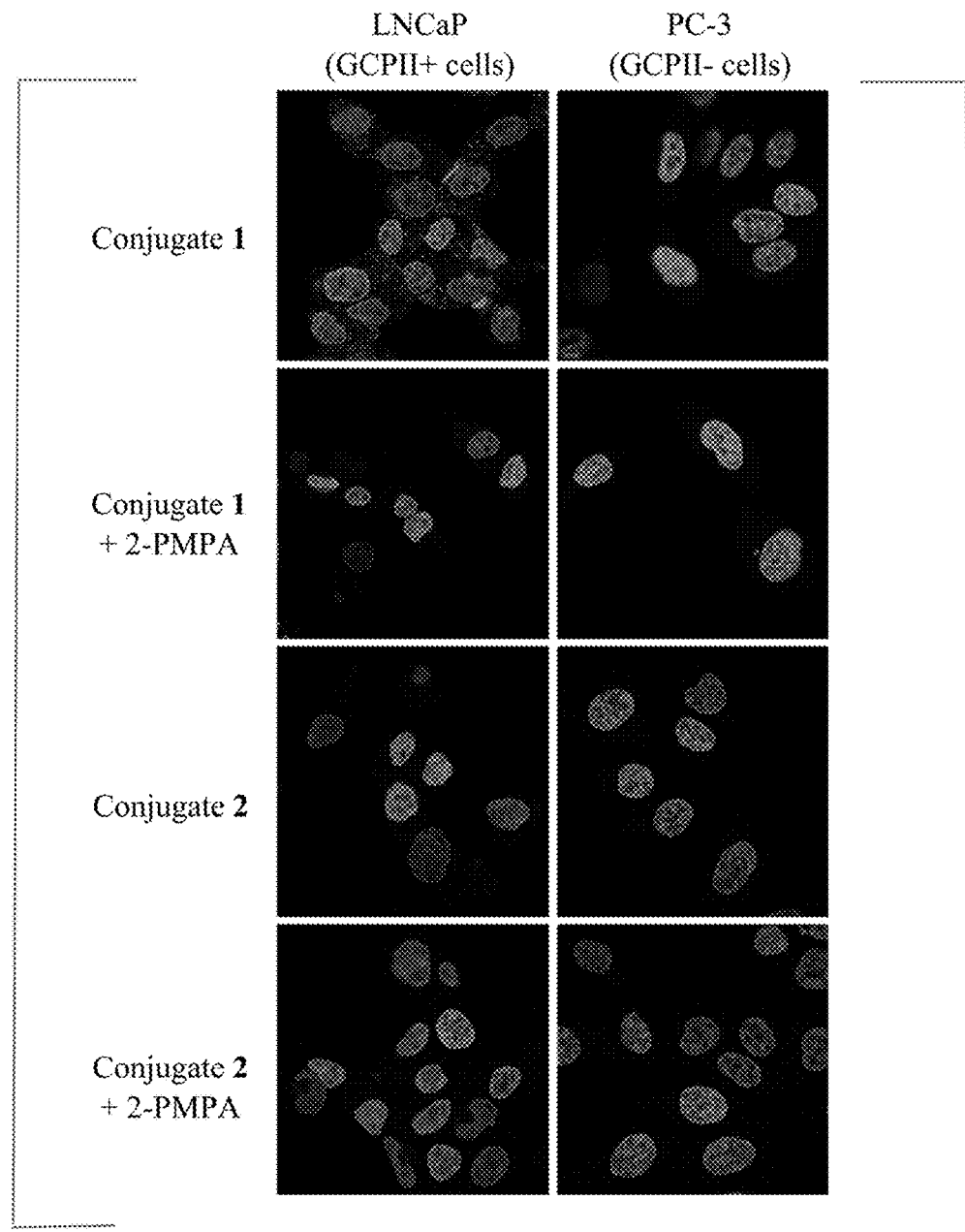
FIG. 14 shows immunocytochemistry using Conjugate 1 and Conjugate 2. LNCaP cells (expressing GCPII) and PC-3 cells (not expressing GCPII) were incubated in the presence of 10 nM Conjugate 1 or Conjugate 2; to verify the selectivity of binding, cells were incubated also in the presence of 10 nM Conjugate 1 or Conjugate 2 and 500 nM 2-PMPA inhibitor. Cell nuclei were stained with Hoechst 33258 and the cells were observed using a Zeiss LSM 780 confocal microscope.

As is evident from FIG. 14, only cells expressing GCPII which were incubated with Conjugate 1 containing inhibitors of GCPII were able to bind and subsequently internalize fluorescent-labeled conjugates. Cells not expressing GCPII, or incubated with conjugate without inhibitors of GCPII, were not capable of interacting with the polymeric conjugates. It was further shown that the presence of 2-PMPA inhibitor competing with the polymer conjugate leads likely to a block of the GCPII active site and therefore to an inability to bind and internalize the polymer conjugates (FIG. 14).

In this application it was demonstrated that polymeric conjugates against GCPII specifically inhibit this enzyme ($K_i$=3.1 pM), and dissociation constant of the binding GCPII-conjugate was determined by SPR ($K_D$<20 pM). Polymeric conjugates were further used to visualize GCPII on the surface and inside the cells by confocal fluorescence microscopy—conjugate binding to GCPII on the cell surface leads to internalization of the complex into the cell. Conjugates worked similarly also in the flow cytometry. Using the polymeric conjugates allowed the isolation of GCPII from various biological samples, like e.g. lysates of cells and tissues, or blood serum and plasma. In combination with anti-GCPII antibody, ELISA sandwich arrangement can detect and quantify the order of picograms and fractions of picograms of GCPII. Thanks to the combination of antibody-conjugate, sandwich ELISA does not suffer from false positive results caused by binding of endogenous interfering antibodies. This can be used for very sensitive and specific quantification of GCPII in biologically relevant samples, e.g. blood, blood plasma, blood serum, cerebrospinal fluid, urine, synovial fluid, amniotic fluid, ascites, pleural fluid, pericardial fluid, saliva, sweat or seminal plasma.

The same conjugate with the same inhibitor selectively binds also into the active site of glutamate carboxypeptidase III (GCPIII), a close homolog of GCPII. When using an antibody selectively binding only GCPIII, ELISA was selective for GCPIII, and GCPII presence did not interfere with the determination. With immobilization through affinity tag and using the same conjugate we managed to detect and quantify the amount of recombinantly prepared proteins GCPII and GCPIII with great sensitivity.

Example 15: Visualization of CA-IX on Cell Surface Using the Polymeric Conjugates (Immunocytochemistry)

Visualization of CA-IX on cell surface (immunocytochemistry) using polymeric conjugates was performed on the HT-29 cell line endogenously expressing CA-IX. Cells were cultured for 48 hours in a medium, to which a solution of Conjugate 3 or Conjugate 2 was then added to a final concentration of 1000 nM and cells were incubated in their presence for 2 hours at 37° C. Subsequently, the medium was removed, cells rinsed with 0.5 ml PBS and incubated with 0.5 mg/ml solution of Hoechst Stain Solution H33258 (Sigma) for 15 minutes to stain cell nuclei. Finally, cells were rinsed with 0.5 ml PBS. Images were acquired using a Zeiss LSM 780 confocal laser microscope (Carl Zeiss, Inc., Oberkochen, Germany) with an oil immersion objective (Plan-Apochromat 63×/1.40 Oil DIC M27). Microscope settings for individual channels were as follows: for Hoechst 33258: excitation 3% of the output of 405 nm diode laser (max. output 30 mW), emission spectral detector range: 410-585 nm; for ATTO488: excitation 3.5% output of 488 nm argon laser (max. output 25 mW), emission spectral detector range: 517-534 nm. Images were processed in ZEN 2011 software (Carl Zeiss Microscopy).

Figure 15:
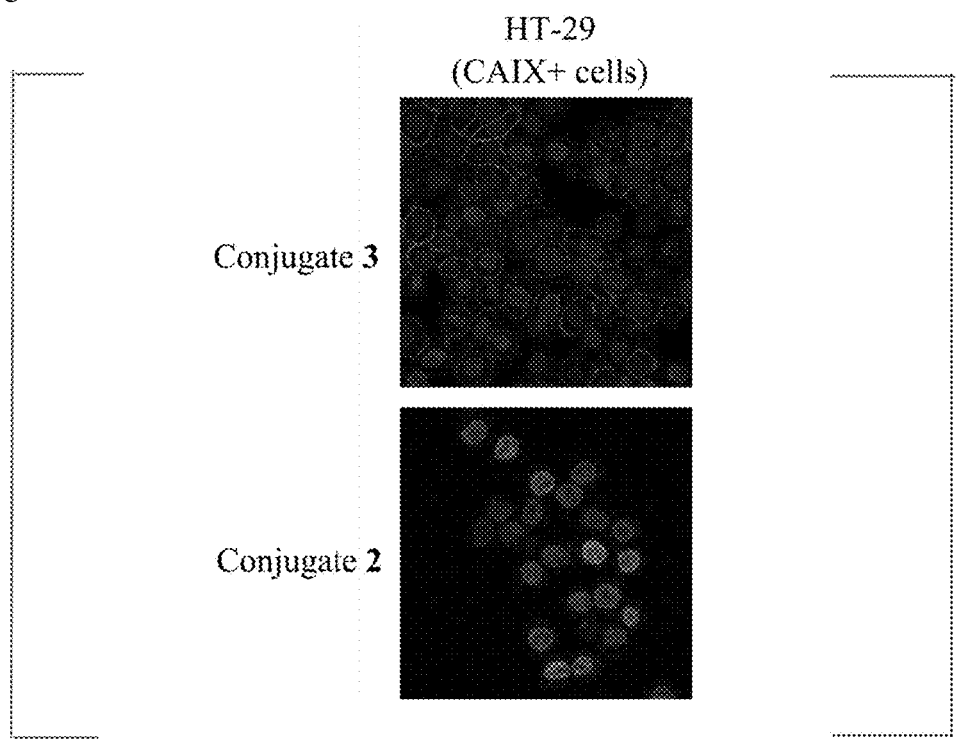
FIG. 15 shows immunocytochemistry using Conjugate 3 and Conjugate 2. HT-29 cells expressing CA-IX were incubated in the presence of 1 µM Conjugate 3 or Conjugate 2. Cell nuclei were stained with Hoechst 33258 and the cells were observed using a Zeiss LSM 780 confocal microscope.

Using immunocytochemistry, it was shown that only Conjugate 3, containing inhibitor of CA-IX, would bind to HT-29 cells expressing CA-IX (FIG. 15). In the experiment, cell membrane was specifically visualized, which is consistent with the fact that CA-IX is a membrane protein.

Example 16: ELISA for the Quantification of CA-IX Using Polymeric Conjugates Sandwich ELISA for quantification of CA-IX was carried out analogously to the ELISA method for GCPII quantification (see Example 11); all steps of the experiment were performed at room temperature.

The plate was first coated with antibody against CA-IX M75 in TBS (500 ng/well, 2 hours). After blocking the surface with casein (18 hr), and its washing away incubation followed with a lysate of HT-29 cells, diluted in 20 mM Tris-HCl, 200 mM NaCl, 0.1% Tween 20, pH 7.4 (TBST') (in amounts of 32 μs-32 ng of total protein/well, 4 hours). A construct containing the catalytic domain and the PG domain of carbonic anhydrase IX (amino acids 55 to 390, hereinafter referred to as CA-IX with PG), which has been prepared by recombinant expression in insect S2 cells and purified as described in [20], was used as standard. After washing with 3×200 μl of TBST, a solution of 5 nM Conjugate 3 in TBST' was added (1 hour), then washed away with 3×200 μl of TBST and NeutrAvidin conjugated to horseradish peroxidase diluted in TBST' (100 ng/well, 30 min, Thermo Scientific) was added to the wells. After washing with 5×200 μl of TBST, chemiluminescent substrate was added and luminescence was measured on a Tecan Infinite M1000 PRO spectrophotometric reader.

For development of the ELISA method for CA-IX quantification, Conjugate 3 was used with an inhibitor selectively binding to the active site of human carbonic anhydrases, especially carbonic anhydrase IX (CA-IX). In combination with the selective immobilization of CA-IX through a monoclonal antibody (in ELISA sandwich arrangement) we achieved a highly sensitive determination of CA-IX in solution and in various biological matrices, particularly in tissue and cell lysates, as well as blood plasma and serum. Like in the case of GCPII, ELISA for the CA-IX quantification with Conjugate 3 allowed detecting picogram quantities of CA-IX; using a combination of M75 antibody (binding CA-IX) and Conjugate and 3, it was possible to detect 1 pg of CA-IX in the HT-29 cell lysate. Thanks to several inhibitors of CA-IX present on one conjugate, it was possible to develop highly sensitive ELISA method using relatively weak (submicromolar) inhibitor of CA-IX. Incubating polymeric conjugate with CA-IX in the presence of test compounds allowed to determine the bond strength (ie. the inhibition constant) of these test substances with great precision.

Example 17: Quantification of the Interactions of the Polymeric Conjugates with CA-IX by Surface Plasmon Resonance (SPR)

Measuring the interaction of the CA-IX protein with Conjugate 3 using surface plasmon resonance (SPR) was performed on four-channel SPR sensor developed at the Institute of Photonics and Electronics AS CR in Prague [16-17]. In a typical experiment, the SPR chip (supplied IPE ASCR) was immersed in ethanol solution of alkanethiols for 1 h at 37° C. (7:3) HS—$(CH_2)_{11}$-$PEG_4$-OH a HS—$(CH_2)_{11}$-$PEG_6$-O—$CH_2$—COOH (Prochimia) at a final concentration of 0.2 mM. The chip was subsequently rinsed with ethanol for UV spectroscopy, with deionized water and dried with nitrogen. Finally, the chip was attached to a SPR chip prism; all measurements were performed at 25° C. Activation of the terminal carboxyl groups on the sensor surface was carried out in situ by addition of a mixture (1:1) 11.51 mg/ml N-hydroxysuccinimide (NHS, Biacore), and 76.68 mg/ml 1-ethyl-3-(3-dimethylaminopropyl)-carbodiimide hydrochloride (EDC, Biacore) in deionized water for 5 min at a flowrate of 20 µl/min. Following parts of the experiment were then performed at a flow rate of 30 µl/min. Subsequently, a solution of NeutrAvidin (20 ng/ml) in 10 mM sodium acetate, pH 5.0, was applied for 8 min. To remove non-specifically bound molecules of NeutrAvidin, a buffer of high ionic strength (PBS with 0.5 M NaCl), was used and then 1 M ethanolamine (Biacore) was applied for deactivation of the remaining activated carboxyl groups. Conjugate 3 containing the inhibitor of CA-IX (1 µM in TBS) was then bound to the immobilized neutravidin (13 min). Finally, a solution of recombinant CA-IX in TBS in varying concentrations was injected on this prepared layer (concentrations of CA-IX were 64, 128, 255 and 510 nM) and subsequently only TBS (dissociation phase).

Figure 16:
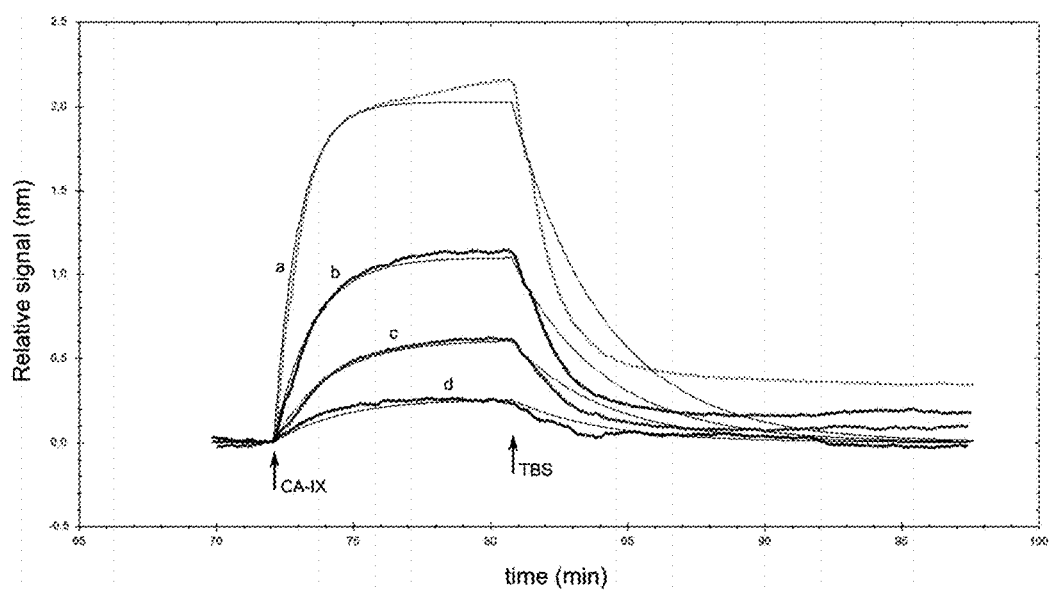
FIG. 16 shows a typical course of binding CA-IX to Conjugate 3 analyzed by SPR (surface plasmon resonance). Conjugate 3 was bound to streptavidin immobilized on a gold chip surface. Four different concentrations of recombinant CA-IX in TBS were then applied to the prepared layer (a) 510 nM; b) 255 nM; c) 128 nM; d) 64 nM) association phase was monitored and then dissociation phase (only TBS application). Acquired curves were processed and then fitted in the TraceDrawer program v.1.5 (Ridgeview Instruments AB, Sweden).

Curves describing the binding (FIG. 16) were exported and analyzed in TraceDrawer v.1.5 (Ridgeview Instruments AB) to obtain the parameters $k_{on}$ and $k_{off}$.

The value of the dissociation constant between CA-DC and Conjugate 3 was determined $K_D$=193 nM; with the value of association rate $k_{on}$=2.64·$10^4$ $M^{-1}s^{-1}$ and $k_{off}$= 5.07$^{-3}$ $s^{-1}$.

Example 18: Affinity Isolation ("Pull-Down") of CA-IX Using Polymeric Conjugates HT29 cells (cultured in 100 mm Petri dish) endogenously expressing CA-IX were lysed by sonication in a water bath (3 min/0° C.) in 450 µl of 50 mM Tris-HCl, 150 mM NaCl, pH 7.4, 1% Tween 20. Resulting cell lysate was further diluted in 20 mM Tris-HCl, 150 mM NaCl, 0.1% Tween 20, pH 7.4 (TBST) to a final protein concentration of 360 µg/ml. Meanwhile, Conjugate 3 and Conjugate 2 (negative control showing nonspecific binding) were pre-bound to 25 µl of Streptavidin Sepharose (200 nM solution in 200 µl of TBST, 1 hour, 6° C.), and after washing with 3×200 µl TBST, the resin was mixed with 200 µl of HT-29 cell lysate and incubated at 25° C. for 3 hours. The resin was then washed with 3×200 µl of TBST and subsequently, proteins were eluted with 25 µl of sample buffer for SDS-PAGE and with heating to 98° C. for 10 min.

To compare the effectiveness of CA-IX isolation with Conjugate 3, CA-IX was also isolated with M75 antibody. The experiment was performed analogously to experiment with polymeric conjugates: 1 µg of antibody was pre-bound to 20 µl of Protein G Sepharose the procedure followed as described above. Protein G Sepharose resin without the antibody was used as negative control.

After isolation, samples were separated by SDS-PAGE electrophoresis and the gel was blotted to a nitrocellulose membrane (wet blot 100 V/1 hour). After transfer of proteins to the membrane, surface of the membrane was blocked with 0.55% (w/v) solution of casein in PBS (Casein Buffer 4×-20× Concentrate, SDT) at room temperature for 1 hour. Then, the blots were incubated with M75 primary antibody for 12 hours at 6° C. (200 ng/ml diluted in 0.55% solution of casein); then the blots were washed three times with PBS containing 0.05% Tween 20 (PBST) and incubated with a secondary goat antibody against murine immunoglobulins conjugated to horseradish peroxidase (Thermo Scientific, diluted in 0.55% casein solution 1: 25000). Finally, the blots were washed three times with PBST, and chemiluminescent substrate SuperSignal West Dura/Femto Chemiluminescent Substrate (Thermo Scientific) was applied to the membrane. Chemiluminescence was recorded with ChemiDoc It™ 600 Imaging System (UVP).

Figure 17:
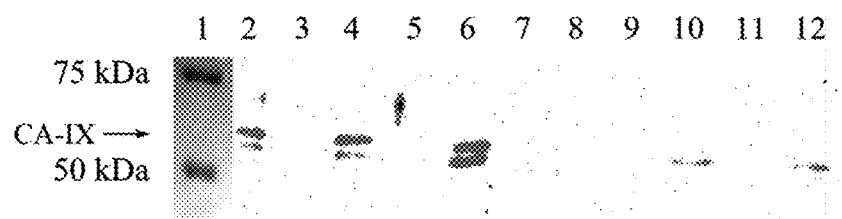
FIG. 17 shows a Western blot demonstrating the affinity isolation of CA-IX ("pull-down") from the lysate of HT-29 cells using Conjugate 3. CA-IX protein was visualized on the membrane using an M75 antibody. Lane 1: All Blue Marker (2 μl); 2: lysate of HT-29 cells (Load); 3: free lane; 4: Elution: Conjugate 3; 5: Elution Elution: Conjugate 2; 6: Elution: M75 antibody; 7: Elution: negative control for M75 antibody; 8: free lane; 9: FT: Elution: Conjugate 3; 10: FT: Conjugate 2; 11: FT: M75 antibody; 12: FT: negative control for M75 antibody. All lanes were loaded with 10 μl of the sample.

With Conjugate 3 it was possible to affinity isolate CA-IX from lysate of HT-29 cells, endogenously expressing CA-IX. Quantities of CA-IX isolated with Conjugate 3 and with M75 antibody prepared against native CA-IX were practically the same (FIG. 17, lanes 4 and 6). Comparative Conjugate 3 serving as a negative control (without CA-IX inhibitor) showed no binding of CA-IX, which shows selective binding of CA-IX to polymeric conjugate through the inhibitor present on Conjugate 3.

Example 19: Modified ELISA Method for Testing CA-IX Inhibitors

The method was carried out analogously to Example 12.

The Maxisorp plate (Nunc) was first coated with M75 antibody in borate buffer (500 ng/well). After blocking the surface with casein and washing it away (see above), incubation followed with recombinant CA-IX (prepared according to [20]) in TBST; 10 ng/well, 1 hr). After washing with 3×200 µl of TBST a solution was added containing either Conjugate 3 alone (5 nM in TBST for 1 hour; Reference sample) or a mixture of Conjugate 3 (5 nM in TBST) and the test substance in the selected concentration (typically 0.1-100 µM in TBST). After incubation for 1 h at room temperature, the wells were washed with 5×200 µl TBST. NeutrAvidin conjugated to horseradish peroxidase was then added to the well (100 ng/well, Thermo Scientific), and after washing with 5×200 µl of TBST, chemiluminescent substrate was added and luminescence was measured on a Tecan Infinite M1000 PRO spectrophotometric reader.

Example 20: Inhibition of HIV-1 Protease Activity with Inhibitors and Conjugates The inhibition analyses were performed by spectrophotometric assay using the chromogenic peptide substrate KARVNle*NphEANle-$NH_2$ as previously described.

The 1 ml reaction mixture contained 100 mM sodium acetate, 300 mM NaCl, pH 4.7, 6.8 pmol of HIV-1 protease and inhibitor in concentrations ranging between 2 and 130 nM. Substrate was added to a final concentration of 16 µM. Afterwards, the hydrolysis of substrate was followed as a decrease in absorbance at 305 nm using a UNICAM UV500 UV-VIS spectrophotometer (Thermo, Cambridge, Mass.). The data were analyzed using the equation for competitive inhibition according to Williams and Morrison. The mechanism of inhibition was determined by analysis of Lineweaver-Burk plots.

Ritonavir is potent and specific inhibitor of HIV-1 protease ($K_i$=15 pM), which is used for AIDS treatment. Therefore, we prepared compound C, which is a ritonavir derivative containing short linker enabling its conjugation with HPMA copolymer. The attachment of the linker did not lead to a significant increase of the inhibition constant ($K_i$=13 pM), a phenomenon observed with GCPII inhibitors. However, the conjugation of compound C to HPMA polymer resulted in a considerable increase of inhibition constant (conjugate 4, $K_i$=7 nM).

Pepstatin A is a potent inhibitor of aspartic proteases, such as HIV-1 protease, pepsin, cathepsin D and cathepsin E. Inhibition constant of pepstatin A towards HIV-1 protease is $K_i$=110 nM; the attachment of the linker to the N-terminus of pepstatin A led to slight increase of the $K_i$ value (compound D, $K_i$=590 nM). Conjugation of compound D to HPMA polymer resulted in a considerable decrease of inhibition constant (conjugate 5, $K_i$=30 nM).

The determined $K_i$ values are shown in the Table 2.

TABLE 2

Prepared inhibitors and polymer conjugates and their inhibition constants towards HIV-1 protease

| Compound | $M_r$ | Targeting | No. of inhibitor moieties | $K_i$ [nM] | Modification |
|---|---|---|---|---|---|
| ritonavir | 721 | HIV-1 protease | — | 0.015 ± 0.002 | — |
| pepstatin A | 686 | aspartic proteases | — | 110 ± 12 | — |
| compound C | 815 | HIV-1 protease | — | 0.012 ± 0.001 | — |
| compound D | 892 | aspartic proteases | — | 590 ± 2 | — |
| Conjugate 4 | 37,000 | HIV-1 protease | 5.3 | 7.2 ± 0.5 | compound C, biotin |
| Conjugate 5 | 71,200 | aspartic proteases | 12.2 | 30.3 ± 0.2 | compound D, biotin |

Example 21: Affinity Isolation ("Pull-Down") of HIV-1 Protease from Spiked LNCaP Lysate Using Conjugates 4 and 5

For isolation of HIV-1 protease, Conjugate 4 (containing ritonavir-based inhibitor) and Conjugate 5 (containing pepstatin A-based inhibitor) were used.

First, 200 nM Conjugate 4 and 5 in 20 mM Tris-HCl, 150 mM NaCl, 0.1% Tween 20, pH 7.4, was bound to 30 µl Streptavidin Agarose Ultra Performance (Solulink) at room temperature for 1 h. Conjugate 2, which lacks the targeting ligand, was used as a negative control. To block unoccupied biotin binding sites, the resin was incubated with 1 ml of 2 mM biotin, 20 mM Tris-HCl, 150 mM NaCl, pH 7.4. Then, the resin was washed three times with 1 ml of 100 mM sodium acetate, 300 mM NaCl, 0.1% Tween 20, pH 4.7. The washed resin was mixed with 200 µl of LNCaP cell lysate spiked with HIV-1 protease (12 ng/µl, total protein concentration 1 mg/ml) in 100 mM sodium acetate, 300 mM NaCl, 0.1% Tween 20, pH 4.7, and incubated for 30 min at room temperature. The resin was washed four times with 1 ml of 100 mM sodium acetate, 300 mM NaCl, 0.1% Tween 20, pH 4.7. Finally, bound HIV-1 protease was eluted from Streptavidin Agarose by adding 30 µl reducing SDS sample buffer and heating to 98° C. for 10 min. Ten microliters of the samples was loaded onto the gel.

Figure 18:
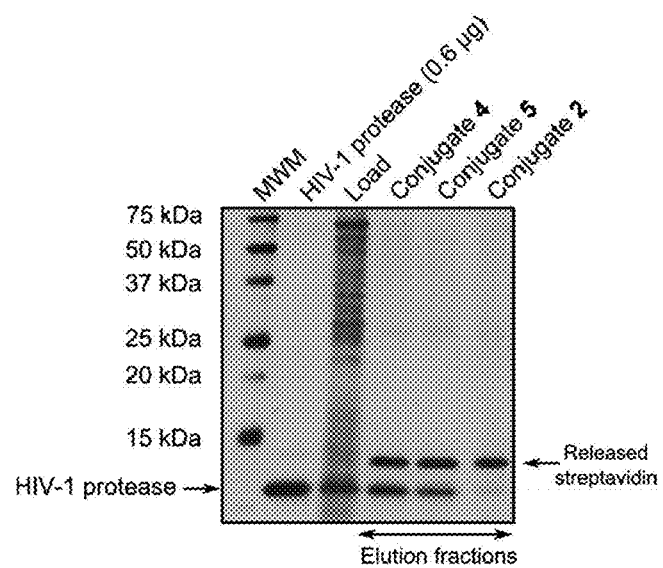
FIG. 18 shows the silver-stained gel demonstrating the affinity isolation of HIV-1 protease ("pull-down") from a LNCaP cell lysate spiked with HIV-1 protease using Conjugate 4 and Conjugate 5. Lane 1: All Blue Marker (0.5 μl); 2: HIV-1 protease standard (600 ng); 3: Load (LNCaP cell lysate spiked with HIV-1 protease); 4: Elution: Conjugate 4; 5: Elution: Conjugate 5; 6: Elution: Conjugate 2 (negative control). Lanes 3-6 were loaded with 10 μl of the sample.

HIV-1 protease is a homodimeric aspartic protease, with an active site located among the monomers. For isolation of HIV-1 protease, Conjugate 4 (containing ritonavir-based inhibitor, i.e. specific HIV-1 protease inhibitor) and Conjugate 5 (containing pepstatin A-based inhibitor, i.e. class specific inhibitor of aspartic proteases) were used. Both conjugate 4 and conjugate 5 specifically bind HIV-1 protease (FIG. 18, lane 4 a 5) and contrastingly, negative control conjugate does not bind HIV-1 protease at all (FIG. 18, lane 6). Intensive 13 kDa band present in the elution fraction of the negative control experiment was identified by mass spectrometry as streptavidin. Streptavidin was probably cleaved off the Streptavidin Sepharose resin by HIV-1 protease, which was not inhibited; in contrast to experiment with conjugate 4 and conjugate 5.

Figure 19:
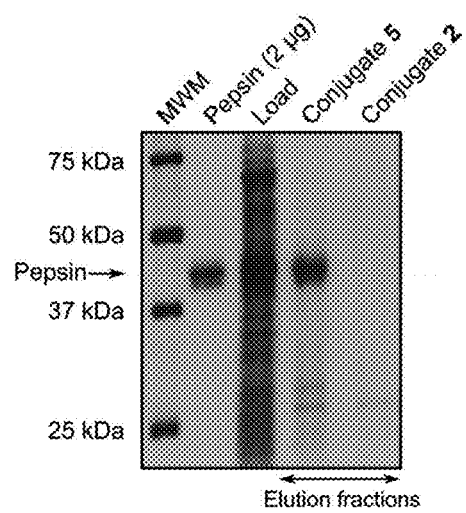
FIG. 19 shows the silver-stained gel demonstrating the affinity isolation of pepsin (the representant of aspartic proteases) from a LNCaP cell lysate spiked with pepsin using Conjugate 5. Lane 1: All Blue Marker (0.5 μl); 2: pepsin standard (2 μg); 3: Load (LNCaP cell lysate spiked with pepsin); 4: Elution: Conjugate 5; 5: Elution: Conjugate 2 (negative control). Lanes 3-5 were loaded with 10 μl of the sample.

To isolate pepsin from the LNCaP cell lysate (spiked with pepsin), Conjugate 5 containing pepstatin A based inhibitor was used. The experiment was performed analogously to the above mentioned isolation of HIV-1 protease (FIG. 19).

INDUSTRIAL APPLICABILITY

Synthetic macromolecular conjugates that are the subject of the present invention can be used in any laboratory and diagnostic applications, where polyclonal or monoclonal antibodies are commonly used, their fragments or derivatives. These can be a cheap and stable substitute of antibodies used in the ELISA diagnostic method (Enzyme-Linked Immunosorbent Assay), as well as in isolation and quantification of biomolecules in complex mixtures (substitute of antibodies in immunoprecipitation), in visualization of tumor markers and other surface molecules (substitute of antibodies in immunohistochemical analysis), and finally substituting antibodies in fluorescent cytometry. In the MRI diagnostic method, for example polymeric conjugate with gadolinium atom intended for in vivo detection can be used.

The invention was developed under the project "Management of the structure and function of biomolecules at the molecular level: the interplay between theory and experiment," Center of Excellence GACR, P208/12/016.

REFERENCES

1. Waldmann, T. A., *Immunotherapy: past, present and future*. Nature Medicine, 2003. 9(3): p. 269-277.
2. http://www.actip.org/pages/monoclonal_antibodies-table.html.
3. Ulbrich, K., et al., *Polymeric drugs based on conjugates of synthetic and natural macromolecules L Synthesis and physico-chemical characterisation*. Journal of Controlled Release, 2000. 64(1-3): p. 63-79.
4. Ulbrich, K. and V. Subr, *Structural and chemical aspects of HPMA copolymers as drug carriers*. Adv Drug Deliv Rev, 2010. 62(2): p. 150-66.
5. Etrych, T., et al., *N-(2-hydroxypropyl)methacrylamide-based polymer conjugates with pH-controlled activation of doxorubicin. I. New synthesis, physicochemical characterization and preliminary biological evaluation*. Journal of Applied Polymer Science, 2008. 109(5): p. 3050-3061.
6. Subr, V., et al., *Synthesis of Well-Defined Semitelechelic Poly[N-(2-hydroxypropyl)methacrylamide] Polymers*

*with Functional Group at the alpha-End of the Polymer Chain by RAFT Polymerization.* Macromolecules, 2013. 46(6): p. 2100-2108.
7. Subr, V. and K. Ulbrich, *Synthesis and properties of new N-(2-hydroxypropyl)-methacrylamide copolymers containing thiazolidine-2-thione reactive groups.* Reactive & Functional Polymers, 2006. 66(12): p. 1525-1538.
8. Kopecek, J., P. Rejmanova, and V. Chytry, *Polymers Containing Enzymatically Degradable Bonds .1. Chymotrypsin Catalyzed-Hydrolysis of Para-Nitroanilides of Phenylalanine and Tyrosine Attached to Side-Chains of Co-Polymers of N-(2-Hydroxypropyl)Methacrylamide.* Makromolekulare Chemie-Macromolecular Chemistry and Physics, 1981. 182(3): p. 799-809.
9. Sacha, P., et al., *Expression of glutamate carboxypeptidase II in human brain.* Neuroscience, 2007. 144(4): p. 1361-72.
10. Murelli, R. P., et al., *Chemical Control over Immune Recognition: A Class of Antibody-Recruiting Small Molecules That Target Prostate Cancer.* Journal of the American Chemical Society, 2009. 131(47): p. 17090-+.
11. Perrier, S., P. Takolpuckdee, and C. A. Mars, *Reversible addition-fragmentation chain transfer polymerization: End group modification for functionalized polymers and chain transfer agent recovery.* Macromolecules, 2005. 38(6): p. 2033-2036.
12. Tykvart, J., et al., *Rational design of urea-based glutamate carboxypeptidase II (GCPII) inhibitors as versatile tools for specific drug targeting and delivery.* Bioorg Med Chem, 2014. 22(15): p. 4099-108.
13. Tykvart, J., et al., *Efficient and versatile one-step affinity purification of in vivo biotinylated proteins: expression, characterization and structure analysis of recombinant human glutamate carboxypeptidase II.* Protein Expr Purif, 2012. 82(1): p. 106-15.
14. Cheng, Y. and W. H. Prusoff, *Relationship between Inhibition Constant (K1) and Concentration of Inhibitor Which Causes 50 Percent Inhibition (150) of an Enzymatic-Reaction.* Biochemical Pharmacology, 1973. 22(23): p. 3099-3108.
15. Knedlik, T., et al., *Detection and quantitation of glutamate carboxypeptidase II in human blood.* Prostate, 2014. 74(7): p. 768-80.
16. Hegnerova, K., et al., *Surface plasmon resonance biosensors for detection of Alzheimer disease biomarker.* Sensors and Actuators B-Chemical, 2009. 139(1): p. 69-73.
17. Pimkova, K., et al., *Surface plasmon resonance biosensor for the detection of VEGFR-1-α protein marker of myelodysplastic syndromes.* Analytical and Bioanalytical Chemistry, 2012. 402(1): p. 381-387.
18. Barinka, C., et al., *Substrate specificity, inhibition and enzymological analysis of recombinant human glutamate carboxypeptidase II.* Journal of Neurochemistry, 2002. 80(3): p. 477-87.
19. Tykvart, J., et al., *Comparative analysis of monoclonal antibodies against prostate-specific membrane antigen (PSMA).* Prostate, 2014.
20. Mader, P., *Structure, Function and Inhibition of Human Carbonic Anhydrases (Ph.D. thesis).* Karlova univerzita v Praze, 2010.

The invention claimed is:

1. A method of identification, visualization, quantification or isolation of proteins and/or cells in vitro or in an immunochemical method, comprising the steps of:
   providing a synthetic macromolecular conjugate adapted for selective interaction with proteins, characterized in that it contains a copolymer to which at least one affinity tag, at least one imaging probe and at least one targeting ligand are bound via covalent bonds,
   wherein said copolymer is a copolymer obtainable by copolymerization of at least one monomer of Formula 1:

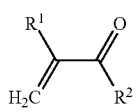 (1)

wherein:
$R^1$ is selected from H, CH$_3$;
$R^2$ is selected from NH$_2$, NH—CH$_2$—CH(OH)—CH$_3$, NH—CH$_3$, NH—CH$_2$CH$_3$, NH—CH$_2$CH$_2$—OH, NH—CH$_2$CH$_2$CH$_2$—OH, NHC(CH$_2$OH)$_3$, NH—CH$_2$CH$_2$—N$^+$(CH$_3$)$_3$Cl$^-$, O—CH$_2$CH$_2$—OH, O—(CH$_2$CH$_2$O)$_2$—H, O—(CH$_2$CH$_2$O)$_3$—H, O—CH$_2$CH$_2$—N$^+$(CH$_3$)$_3$Cl$^-$, NH—(CH$_2$)$_3$N$^+$(CH$_3$)$_2$—(CH$_2$)$_2$—COO$^-$; and
at least one monomer of Formula 2:

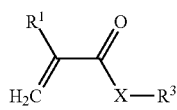 (2)

wherein:
$R^1$ is selected from H, CH$_3$, and
X is selected from NH—(CH$_2$)$_2$—CO, NH—(CH$_2$)$_3$—CO, NH—(CH$_2$)$_4$—CO, NH—(CH$_2$)$_5$—CO, Gly, GlyGly, GlyPheLeuGly, and
$R^3$ is selected from

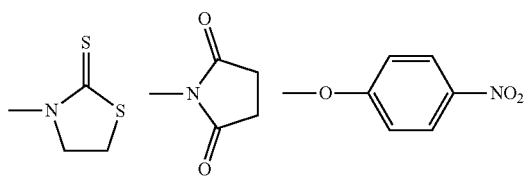

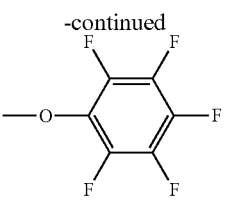

whereas at least one reactive group $R^3$ is replaced by the targeting ligand, at least one reactive group $R^3$ is replaced by the affinity tag, and at least one reactive group $R^3$ is replaced by the imaging probe; and
binding to a target protein and/or cells a synthetic macromolecular conjugate, which contains a copolymer to which at least one affinity tag, wherein at least one imaging probe and at least one targeting ligand are bound via covalent bonds; and
a step of identification, visualization, quantification or isolation of the target protein and/or cell using the affinity tag and/or the imaging probe of the macromolecular conjugate.

2. The method according to claim 1, wherein the molecular weight of the conjugate is in the range of 1000 to 500000 g/mol.

3. The method according to claim 1, wherein the targeting ligand is a moiety capable of selectively binding to the target protein, wherein the targeting ligand is selected from the group consisting of an inhibitor or substrate of the targeted enzyme, an agonist or antagonist of the targeted receptor, and a ligand of the target protein resin.

4. The method according to claim 1, wherein the targeting ligand may be attached to the synthetic copolymer via a linker, a peptide, a nucleic acid, or an oligosaccharide.

5. The method according to claim 1, wherein the affinity tag is selected from biotin, His-tag, FLAG tag, HA tag, Strep-tag, Avi-Tag, GST-tag, c-myc-tag, V5-tag, E-tag, S-tag, SBP-tag, poly(Glu)-tag, and calmodulin.

6. The method according to claim 1, wherein the imaging probe is selected from the group comprising fluorescent moieties, radionuclides and metal complexes.

7. The method according to claim 6, wherein the imaging probe is selected from the group consisting of fluorophores with an excitation maximum in the range of 350 to 850 nm, lanthanide complexes, and radionuclide complexes $^{64}$Cu, $^{68}$Ga, $^{18}$F, $^{99m}$Tc, $^{123}$I, $^{125}$I, $^{131}$I, $^{57}$Co, $^{51}$Cr, $^{67}$Ga, $^{64}$Cu, $^{111}$In, $^{90}$Y.

8. The method according to claim 1 wherein the method of identification, visualization, quantification or isolation is an immunochemical method selected from the group consisting of ELISA, flow cytometry, immunocytochemistry, immunohistochemistry, Wester blotting and modifications thereof.

9. The method according to claim 1, wherein the target protein is GCPII, GCPIII, CA-II, CA-VII, CA-IX, HIV-1 protease, or aspartate protease.

* * * * *